United States Patent [19]

Heath, Jr. et al.

[11] Patent Number: 5,672,618
[45] Date of Patent: Sep. 30, 1997

[54] PROTEIN KINASE C INHIBITORS

[75] Inventors: William F. Heath, Jr., Fishers; John H. McDonald, III, Carmel, both of Ind.; Michael Paal, Hamburg, Germany; Theo Schotten, Vierhöfen, Germany; Wolfgang Stenzel, Reinbek, Germany

[73] Assignee: Eli Lilly and Company, Indianapolis, Ind.

[21] Appl. No.: 452,606

[22] Filed: May 25, 1995

Related U.S. Application Data

[60] Division of Ser. No. 324,948, Oct. 18, 1994, Pat. No. 5,545,636, which is a continuation-in-part of Ser. No. 173,741, Dec. 23, 1993, abandoned.

[51] Int. Cl.$^6$ .......... A61K 31/40; A61K 31/70; C07D 401/14; C07H 17/00
[52] U.S. Cl. .......... 514/414; 514/411; 514/32; 548/428; 548/455; 548/466; 536/17.3
[58] Field of Search .......... 536/17.3; 548/428, 548/466, 455; 514/411, 414, 32

[56] References Cited

U.S. PATENT DOCUMENTS

| | | | |
|---|---|---|---|
| 4,785,085 | 11/1988 | Kaneko et al. | 536/23 |
| 4,808,613 | 2/1989 | Kaneko et al. | 514/42 |
| 4,923,986 | 5/1990 | Murakata et al. | 540/545 |
| 5,057,614 | 10/1991 | Davis et al. | 548/466 |
| 5,292,747 | 3/1994 | Davis et al. | 514/285 |
| 5,380,746 | 1/1995 | Barth et al. | 514/414 |
| 5,481,003 | 1/1996 | Gillig | 548/455 |

FOREIGN PATENT DOCUMENTS

| | | | |
|---|---|---|---|
| 3914764 A1 | 11/1990 | Denmark | 403/14 |
| 0 434 057 A2 | 12/1990 | Denmark | 487/14 |
| 0 269 025 A2 | 11/1987 | European Pat. Off. | 19/44 |
| 0 470 490 A1 | 7/1991 | European Pat. Off. | 471/4 |
| 0 540 956 A1 | 10/1992 | European Pat. Off. | 471/14 |
| 0 624 586 A1 | 11/1994 | European Pat. Off. | 471/4 |
| 0 328 000 A2 | 2/1989 | Germany | 487/14 |
| 0 384 349 A1 | 2/1990 | Germany | 403/4 |
| 0 397 060 A2 | 5/1990 | Germany | 403/14 |
| WO 91/13070 | 9/1991 | WIPO | 403/4 |
| WO 91/13071 | 9/1991 | WIPO | 403/14 |
| WO 94/02488 | 2/1994 | WIPO | 498/22 |
| WO 94/14798 | 7/1994 | WIPO | 403/14 |

OTHER PUBLICATIONS

Thomas et al. "Dioctanoylglycerol regulation of cytosolic CA by protein kinase C–indipendent mechanism in HIT T–15 islet cells" Diabetes vol. 40, pp. 621–627 (1991).

Dominique et al. "The bisindolylmaleimide GF 109203X is a potent and selective inhibitor of protein kinase C" Jo. Biolo. Chem. vol. 266 (24) pp. 15771–15781 (1991).

Davis et al. "Preparation of 3–(3–indolyl)pyrrole–2,5–diones and analogs as protein kinase inhibitors" CA 112:98378 (1990).

Derwent Abstract 90–132947/18; (1988) DE–835842.

Derwent Abstract 92–274042/33; (1990) 90JP–314628.

Meier, e al., *Tetrahedron Letters*, 34:33, 5277–5280 (1993).

Wilkinson, et al., *Bichem. J.*, 294, 335–337 (1993).

Bit, et al., *J. Med. Chem.*, 36, 21–29 (1993).

Martiny–Baron, et al., *The Journal of Biological Chemistry*, 268:13, 9194–9197 (1993).

Krakowiak, et al, *Synlett*, 611–620, (Sep. 1993).

Mulqueen, et al., *Agents Actions*, 37, 85–89 (1992).

Davis, et al., *J. Med. Chem.*, 35, 177–184 (1992).

Davis, et al., *J. Med. Chem.*, 35, 994–1001 (1992).

Nixon, et al., *Drugs Exptl. Clin. Res.*, 17:8, 389–393 (1991).

Davis, et al., *Tetrahedron Letters*, 31:36, 5201–5204 (1990).

Brenner, et al., *Tetrahedron Letters*, 44:10, 2887–2892 (1988).

Joyce, et al., *The Journal of Organic Chemistry*, 52:7, 1177–1186 (1987).

Buchdunger, et al., *Proc. Natl. Acad. Sci. USA*, 91, 2334–2338 (Mar. 1994).

Kobayashi, et al., *The American Physiological Society*, 0363–6135, H1214–H1220 (1994).

Felsenstein, et al., *Neuroscience Letters*, 174 173–176 (1994).

Demaerschalck, et al., *Biochimica et Biophysica Acta*, 1181 214–218 (1993).

Shimohama, et al., *Neurology*, 43 1407–1413 (1993).

*Primary Examiner*—Ceila Chang
*Attorney, Agent, or Firm*—Steven P. Caltrider; David E. Boone; Daniel W. Collins

[57] ABSTRACT

The present invention discloses compounds that are highly isozyme selective protein kinase C beta-1 and beta-2 isozyme inhibitors. Accordingly, the present invention provides a method of selectively inhibiting protein kinase C isozymes beta-1, and beta-2. As isozyme selective inhibitors of beta-1 and beta-2, the compounds are therapeutically useful in treating conditions associated with diabetes mellitus and its complications, as well as other disease states associated with an elevation of the beta-1 and beta-2 isozyme.

6 Claims, No Drawings

PROTEIN KINASE C INHIBITORS

This application is a division of application Ser. No. 08/324,948 filed Oct. 18, 1994, now U.S. Pat. No. 5,545,636 which is a continuation-in-part of Heath, et al., U.S. Ser. No. 08/173,741, filed Dec. 23, 1993, now abandoned.

BACKGROUND OF THE INVENTION

Protein kinase C (PKC) consists of a family of closely related enzymes that function as serine/threonine kinases. Protein kinase C plays an important role in cell-cell signaling, gene expression, and in the control of cell differentiation and growth. At present, there are currently at least ten known isozymes of PKC that differ in their tissue distribution, enzymatic specificity, and regulation. Nishizuka Y. *Annu. Rev. Biochem.* 58: 31-44 (1989); Nishizuka Y. *Science* 258: 607-614 (1992).

Protein kinase C isozymes are single polypeptide chains ranging from 592 to 737 amino acids in length. The isozymes contain a regulatory domain and a catalytic domain connected by a linker peptide. The regulatory and catalytic domains can be further subdivided into constant and variable regions. The catalytic domain of protein kinase C is very similar to that seen in other protein kinases while the regulatory domain is unique to the PKC isozymes. The PKC isozymes demonstrate between 40-80% homology at the amino acid level among the group, however, the homology of a single isozyme between different species is generally greater than 97%.

Protein kinase C is a membrane-associated enzyme that is allosterically regulated by a number of factors, including membrane phospholipids, calcium, and certain membrane lipids such as diacylglycerols that are liberated in response to the activities of phospholipases. Bell, R. M. and Burns, D. J., *J. Biol. Chem.* 266: 4661-4664 (1991); Nishizuka, Y. *Science* 258: 607-614 (1992). The protein kinase C isozymes, alpha, beta-1, beta-2 and gamma, require membrane phospholipid, calcium and diacylglycerol/phorbol esters for full activation. The delta, epsilon, eta, and theta forms of PKC are calcium-independent in their mode of activation. The zeta and lambda forms of PKC are independent of both calcium and diacylglycerol and are believed to require only membrane phospholipid for their activation.

Only one or two of the protein kinase C isozymes may be involved in a given disease state. For example, the elevated blood glucose levels found in diabetes lead to an isozyme-specific elevation of the beta-2 isozyme in vascular tissues. Inoguchi et al., *Proc. Natl. Acad. Sci. USA* 89: 11059-11065 (1992). A diabetes-linked elevation of the beta isozyme in human platelets has been correlated with their altered response to agonists. Bastyr III, E. J. and Lu, J. *Diabetes* 42: (Suppl 1) 97A (1993). The human vitamin D receptor has been shown to be selectively phosphorylated by protein kinase C beta. This phosphorylation has been linked to alterations in the functioning of the receptor. Hsieh et al., *Proc. Natl. Acad. Sci. USA* 88: 9315-9319 (1991); Hsieh et al., *J. Biol. Chem.* 268: 15118-15126 (1993). In addition, recent work has shown that the beta-2 isozyme is responsible for erythroleukemia cell proliferation while the alpha isozyme is involved in megakaryocyte differentiation in these same cells. Murray et al., *J. Biol. Chem.* 268: 15847-15853 (1993).

The ubiquitous nature of the protein kinase C isozymes and their important roles in physiology provide incentives to produce highly isozyme selective PKC inhibitors. Given the evidence demonstrating linkage of certain isozymes to disease states, it is reasonable to assume that inhibitory compounds that are selective to one or two protein kinase C isozymes relative to the other PKC isozymes are superior therapeutic agents. Such compounds should demonstrate greater efficacy and lower toxicity by virtue of their specificity.

Compounds are known to be protein kinase C inhibitors. Some are also known to demonstrate specificity to protein kinase C. However, very little is known regarding isozyme selectivity. Studies of the PKC-selective compound, 3-[1-(3-dimethylaminopropyl)-indol-3-yl]-4-(1H-indol-3-yl)-1H-pyrrole-2,5-dione, suggest a slight selectivity for the calcium dependent isozymes, but find no isozyme selectivity between alpha, beta-1, beta-2, and gamma. Toullec et al., *J. Biol. Chem.* 266: 15771-15781 (1991). Martiny-Baron, et al., *J. Biol. Chem.* 268: 9194-9197 (1993), tested the same compound and found slight selectivity for isozymes, alpha and beta versus delta, epsilon, and zeta. Martiny-Baron observed no differences in the selectivity between alpha and beta-1 isozymes. Wilkinson, et al., *Biochem. J.* 294: 335-337 (1993), failed to observe any high degree of isozyme selectivity and suggest only slight selectivity for the alpha isozyme and equal inhibition of beta, gamma, and epsilon for several species of bis-indolemaleimides. Therefore, despite years of research, there remains a need for therapeutically effective isozyme-selective inhibitors.

This invention provides the unexpected discovery that the compounds of the present invention are highly isozyme selective. The compounds selectively inhibit protein kinase C beta-1 and beta-2 isozymes. Accordingly, the present invention provides a method of selectively inhibiting protein kinase C isozymes beta-1 and beta-2. As isozyme selective inhibitors of beta-1 and beta-2, the compounds are therapeutically useful in treating conditions associated with diabetes mellitus and its complications, as well as other disease states associated with an elevation of the beta-1 and beta-2 isozymes.

SUMMARY OF THE INVENTION

This invention provides a method of selectively inhibiting protein kinase C beta-1 and beta-2 isozyme, which comprises administering to a mammal in need of such treatment a pharmaceutically effective amount of a compound of the Formula I:

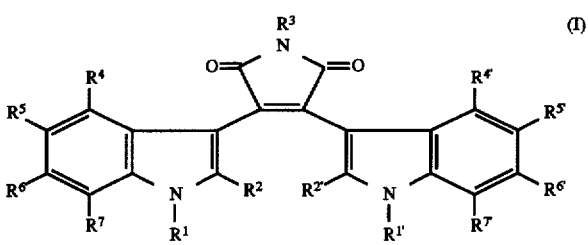

wherein:

$R^1$ and $R^{1'}$ are independently hydrogen, alkyl, haloalkyl, alkenyl, arylalkyl, alkoxyalkyl, hydroxyalkyl, aminoalkyl, monoalkylaminoalkyl, dialkylaminoalkyl, acylaminoalkyl, acyloxyalkyl, cyanoalkyl, amidinoalkyl, carboxyalkyl, alkoxycarbonylalkyl, aminocarbonylalkyl, or a group of the formula:

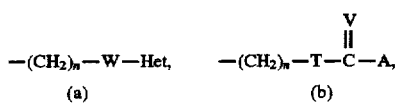
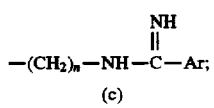

Het signifies a heterocyclyl group;

W signifies NH, S or a bond;

T signifies NH or S;

V signifies O, S, NH, or NCN;

A signifies alkylthio, amino, monoalkylamino or dialkylamino;

Ar signifies aryl;

$R^2$ and $R^{2'}$ are independently hydrogen, alkyl, alkoxyalkyl, hydroxyalkyl, $C_1$-$C_3$ alkylthio, S(O) $C_1$-$C_3$ alkyl, $CF_3$; or $R^1$ and $R^2$ can combine to form $-(CH_2)_r-X-CH2-$;

$R^3$ is hydrogen or $CH_3CO$;

$R^4$, $R^{4'}$, $R^5$, $R^{5'}$, $R^6$, $R^{6'}$, $R^7$ and $R^{7'}$ are independently hydrogen, halogen, alkyl, hydroxy, alkoxy, —COO ($C_1$-$C_3$ alkyl), $CF_3$, nitro, amino, acetylamino, monoalkylamino, dialkylamino, alkylthio, $C_1$-$C_3$ alkylthio, or S(O)$C_1$-$C_3$ alkyl;

X is $CHR^8$ or $NR^8$;

$R^8$ is $(CH_2)_s R^9$;

$R^9$ is hydrogen, hydroxy, alkoxy, amino, monoalkylamino, dialkylamino, trialkylamino, azido, acylamino, alkoxycarbonyl, cyano, amidino, or aminocarbonyl;

n is 1, 2, 3, 4, 5 or 6;

r is 1, 2, or 3; and s is 0, 1, 2 or 3.

As selective inhibitors, the invention further provides a method for treating diabetes mellitus, which comprises administering to a mammal in need of such treatment a pharmaceutically effective amount of a compound of the Formula I.

In addition, the present invention provides novel compounds, which are isozyme selective PKC inhibitors, of the Formulas II, III, and IV:

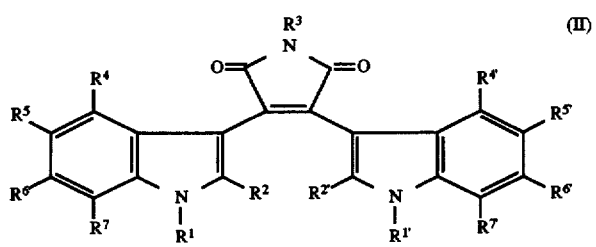
(II)

wherein:

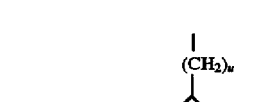
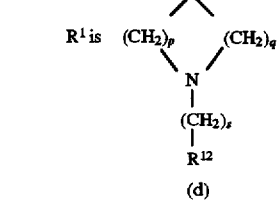
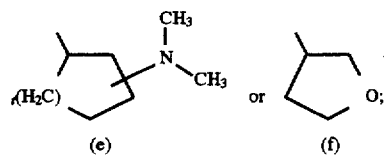

(d) (e) (f)

$R^{1'}$ is hydrogen, $C_1$-$C_4$ alkyl, aminoalkyl, monoalkylaminoalkyl, or dialkylaminoalkyl;

$R^2$ and $R^{2'}$ are independently hydrogen, alkyl, alkoxyalkyl, hydroxyalkyl, $C_1$-$C_3$ alkylthio, S(O) $C_1$-$C_3$ alkyl, $CF_3$;

$R^3$ is hydrogen or $CH_3CO$—;

$R^4$, $R^{4'}$, $R^5$, $R^{5'}$, $R^6$, $R^{6'}$, $R^7$ and $R^{7'}$ are independently hydrogen, halogen, alkyl, hydroxy, alkoxy, —COO ($C_1$-$C_3$ alkyl), $CF_3$, nitro, amino, acetylamino, monoalkylamino, dialkylamino, alkylthio, $C_1$-$C_3$ alkylthio, or S(O)$C_1$-$C_3$ alkyl;

$R^{12}$ is hydrogen, alkyl, haloalkyl, cycloalkyl, acetyl, aryl, —CH(aryl)$_2$, amino, monoalkylamino, dialkylamino, guanidino, —C(=N(alkoxycarbonyl))NH (alkyoxycarbonyl), amidino, hydroxy, carboxy, alkoxycarbonyl or heterocyclyl;

p and q are independently 1, 2, 3, or 4;

s is 0, 1, 2 or 3;

t is 1 or 2;

u is 0 or 1; or pharmaceutically acceptable salts or solvates thereof.

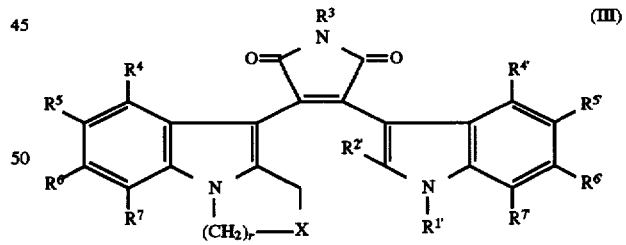
(III)

wherein:

$R^{1'}$ is hydrogen, $C_1$-$C_4$ alkyl, aminoalkyl, monoalkylaminoalkyl, or dialkylaminoalkyl;

$R^{2'}$ is hydrogen, alkyl, alkoxyalkyl, hydroxyalkyl, $C_1$-$C_3$ alkylthio, S(O)$C_1$-$C_3$ alkyl, $CF_3$;

$R^3$ is hydrogen or $CH_3CO$—;

$R^4$, $R^{4'}$, $R^5$, $R^{5'}$, $R^6$, $R^{6'}$, $R^7$ and $R^{7'}$ are independently hydrogen, halogen, alkyl, hydroxy, alkoxy, —COO ($C_1$-$C_3$ alkyl), $CF_3$, nitro, amino, acetylamino, monoalkylamino, dialkylamino, alkylthio, $C_1$-$C_3$ alkylthio, or S(O)$C_1$-$C_3$ alkyl;

X is $CR^8R^9$;

$R^8$ is $(CH_2)_rR^{10}$;

$R^9$ is $(CH_2)_sR^{11}$;

$R^{10}$ and $R^{11}$ are independently hydroxy, alkoxy, carboxy, acyloxy, amino, monoalkylamino, dialkylamino, trialkylamino, azido, acylamino, alkoxycarbonyl, cyano, amidino, or aminocarbonyl;

r is 1, 2, or 3;

s is 0, 1, 2 or 3; or pharmaceutically acceptable salts or solvates thereof.

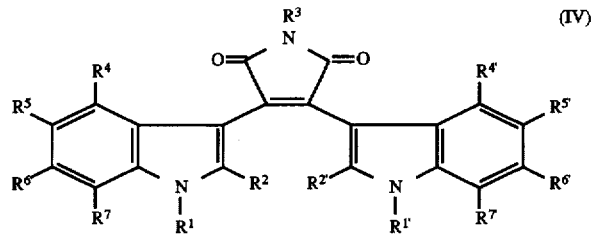
(IV)

wherein:

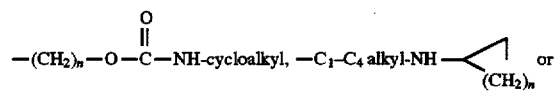

$R^1$ is alkylglycose residue;

$R^{1'}$ is hydrogen, $C_1-C_4$ alkyl, cyclopropylmethyl, aminoalkyl, monoalkylaminoalkyl, or dialkylaminoalkyl;

$R^2$ and $R^{2'}$ are independently hydrogen, alkyl, alkoxyalkyl, hydroxyalkyl, $C_1-C_3$ alkylthio, S(O) $C_1-C_3$ alkyl, $CF_3$;

$R^3$ is hydrogen or $CH_3CO$—;

$R^4$, $R^{4'}$, $R^5$, $R^{5'}$, $R^6$, $R^{6'}$, $R^7$ and $R^{7'}$ are independently hydrogen, halogen, alkyl, hydroxy, alkoxy, —COO ($C_1-C_3$ alkyl), $CF_3$, nitro, amino, acetylamino, monoalkylamino, dialkylamino, alkylthio, $C_1-C_3$ alkylthio, or $S(O)C_1-C_3$ alkyl;

n is 1, 2, 3, 4, 5 or 6; or pharmaceutically acceptable salts or solvates thereof.

DETAILED DESCRIPTION AND PREFERRED EMBODIMENTS

As noted above, the invention provides compounds of the Formula I which selectively inhibit isozymes of protein kinase C.

The preferred compounds of this invention are those compounds of the Formula Ia and Ib:

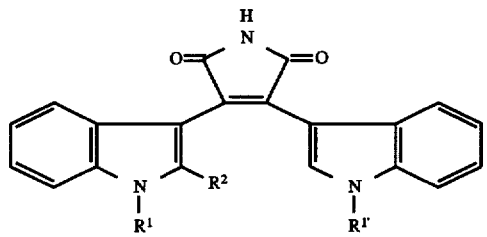
(Ia)

wherein:

$R^1$ is hydrogen, aminoalkyl, monoalkylaminoalkyl, dialkylaminoalkyl;

$R^{1'}$ is hydrogen, $C_1-C_4$ alkyl, aminoalkyl, monoalkylaminoalkyl, or dialkylaminoalkyl; and $R^2$ is hydrogen or methyl.

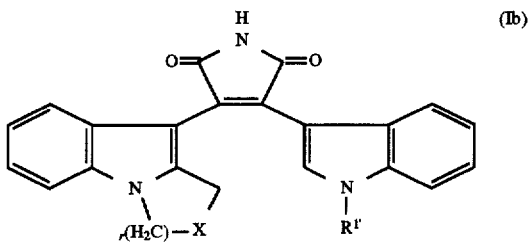
(Ib)

$R^{1'}$ is hydrogen or $C_1-C_4$ alkyl;

X is $CR^8R^9$ or $NR^8$;

$R^8$ is $(CH_2)_rR^{10}$;

$R^9$ is $(CH_2)_sR^{11}$;

$R^{10}$ and $R^{11}$ are independently hydrogen, hydroxy, amino, monoalkylamino, or dialkylamino;

r is 1 or 2; and s is 1.

As previously noted, some of the compounds of the present invention are novel. The preferred novel compounds of the present invention are compounds of the Formula II wherein u is 0. The most preferred novel compounds of Formula II are of the Formula (IIa):

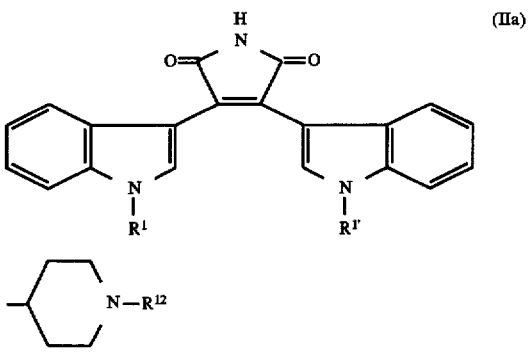
(IIa)

wherein:

$R^1$ is $R^{1'}$ is hydrogen, or $C_1-C_4$ alkyl; and $R^{12}$ is hydrogen, or $C_1-C_4$ alkyl.

Other preferred novel compounds of the present invention are compounds of the Formula IIIa:

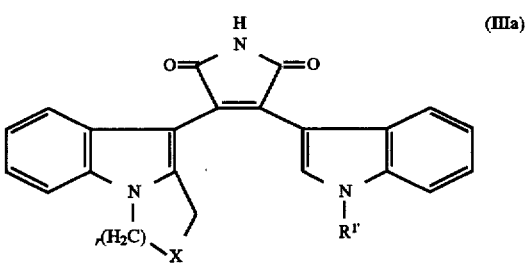
(IIIa)

wherein

R1' is hydrogen, alkyl, aminoalkyl, monoalkylaminoalkyl, or dialkylaminoalkyl;

X is $CR^8R^9$;

$R^8$ is $(CH_2)_rR^{10}$;

$R^9$ is $(CH_2)_sR^{11}$;

$R^{10}$ and $R^{11}$ are independently hydroxy, carboxy, alkoxycarbonyl, amino, monoalkylamino, or dialkylamino;

r is 1 or 2; and s is 0 or 1.

As used herein, the term "alkyl", alone or in combinations, means a straight or branched-chain alkyl group containing from one to seven, preferably one to four, carbon atoms such as methyl, ethyl, propyl, isopropyl, butyl, sec-butyl, t-butyl and pentyl. The term "$C_1$-$C_4$ alkyl" is an alkyl limited to one to four carbon atoms.

The term "cycloalkyl", alone or in combinations, means a three to seven carbon cycloalkyl, for example, cyclopropyl, cyclobutyl, cyclopentyl, cyclohexyl, and cycloheptyl.

The term "alkenyl" means a two to seven carbon, straight or branched hydrocarbon containing one or more double bonds, preferably one or two double bonds. Examples of alkenyl include ethenylene, propenylene, 1,3 butadienyl, and 1,3,5-hexatrienyl.

The term "alkoxy", alone or in combinations, is an alkyl covalently bonded by an —O— linkage. Examples of alkoxy groups are methoxy, ethoxy, propoxy, isopropoxy, butoxy and t-butoxy. An alkoxyalkyl is, for example, $CH_3$($CH_2$)—O—($CH_2$)$_m$— wherein m is the from one to seven or preferably one to four. The term alkoxycarbonyl is, for example, t-butoxycarbonyl or BOC.

A haloalkyl group is an alkyl with one or more, preferably one to three halogen atoms, examples of such group $CH_2Cl$, $CF_3$, $CH_2CF_3$, $CH_2(CF_2)_2CF_3$, and the like.

The acyl moiety of an acylamino or acylaminoalkyl group is derived from an alkanoic acid containing a maximum of 7, preferably a maximum of 4, carbon atoms (e.g. acetyl, propionyl or butyryl) or from an aromatic carboxylic acid (e.g. benzoyl). An acyloxy is one such acyl bonded by an —O— linkage, for example, acetyloxy, $CH_3C(=O)O$—. An acylamino is, for example, $CH_3(C=O)NH$— (acetylamino). Likewise, an acylaminoalkyl is $CH_3(C=O)NH(CH_2)_m$—.

The term "aryl", alone or in combinations means an unsubstituted phenyl group or a phenyl group carrying one or more, preferably one to three, substituents, independently selected from halogen, alkyl, hydroxy, benzyloxy, alkoxy, haloalkyl, nitro, amino, acylamino, monoalkylamino, dialkylamino, alkylthio, alkylsulfinyl, alkylsulfonyl and cyano. The term arylalkyl is preferably benzyl.

The term "halogen" means fluorine, chlorine, bromine or iodine.

The heterocyclic group denoted by "Het" or "heterocyclyl" can be a stable, saturated, partially unsaturated, or aromatic 5- or 6-membered heterocyclic group. The heterocyclic ring consists of carbon atoms and from one to three heteroatoms independently selected from the group consisting of nitrogen, oxygen, and sulfur. The heterocyclic group can be optionally substituted with one to three substituents independently selected from halogen, alkyl, hydroxy, alkoxy, haloalkyl, nitro, amino, acylamino, monoalkylamino, dialkylamino, alkylthio, alkylsulfinyl and alkylsulfonyl or, when the heterocyclyl group is an aromatic nitrogen-containing heterocyclic group, the nitrogen atom can carry an oxide group. Examples of such heterocyclyl groups are imidazolyl, imidazolinyl, thiazolinyl, pyridyl, indolyl, furyl, and pyrimidinyl.

The term "alkylglycose residue" represents a glycose moiety linked in the C-1 position to the indolyl via a $C_2$-$C_4$ alkyl. Glycoses included in alkylglycose residue are natural or unnatural 5 or 6 carbon sugars, preferably selected from allosyl, altrosyl, glucosyl, mannosyl, gulosyl, idosyl, galactosyl, talosyl, arabinosyl, xylosyl, lyxosyl, rhamnosyl, ribosyl, deoxyfuranosyl, deoxypyranosyl, and deoxyribosyl. The glycose may be azide substituted, O-acetylated, O-methylated, amino, mono, and di-alkylamino substituted, or acylamino substituted. For example, alkylglycose residue includes:

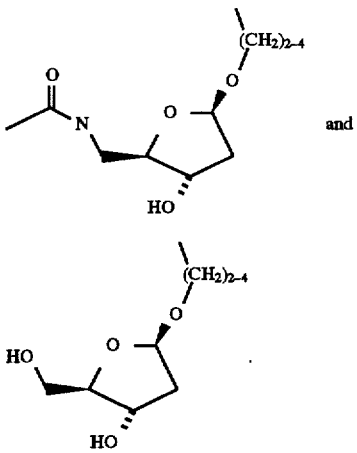

The term "pharmaceutically effective amount", as used herein, represents an amount of a compound of the invention that is capable of selectively inhibiting PKC isozyme activity in mammals. The particular dose of the compound administered according to this invention will, of course, be determined by a physician under the particular circumstances surrounding the case, including the compound administered, the route of administration, the particular condition being treated, and similar considerations. The compounds can be administered by a variety of routes including the oral, rectal, transdermal, subcutaneous, topical, intravenous, intramuscular or intranasal routes.

The term "treating," as used herein, describes the management and care of a patient for the purpose of combating the disease, condition, or disorder and includes the administration of a compound of present invention to prevent the onset of the symptoms or complications, alleviating the symptoms or complications, or eliminating the disease, condition, or disorder.

The term "isozyme selective" means the preferential inhibition of protein kinase C beta-1 or beta-2 isozymes over protein kinase C isozymes, alpha, gamma, delta, epsilon, zeta, and eta. In general, the compounds demonstrate a minimum of a eight fold differential, preferably ten fold differential, in the dosage required to inhibit PKC beta-1 or beta-2 isozymes and the dosage required for equal inhibition of the alpha protein kinase C isozyme as measured in the PKC assay. The compounds demonstrate this differential across the range of inhibition and are exemplified at the $IC_{50}$, i.e., a 50% inhibition. Accordingly, the invention provides a method for selectively inhibiting the beta-1 or beta-2 protein kinase C isozyme. A related phrase is "selectively inhibiting protein kinase C beta-1 and beta-2 isozymes," which refers to isozyme selective inhibition. Thus, because one needs a substantially higher concentration of compound to inhibit the other protein kinase C isozymes (e.g., Example 11 discloses 50% inhibition at a concentration of 0.046 µmol/L for the beta-2 protein kinase C isozyme while the $IC_{50}$ with respect to the alpha protein kinase C isozyme is 0.45 µmol/L), a pharmaceutically effective dosage of the compound inhibits beta-1 and beta-2 protein kinase C isozymes with lower toxicity by virtue of their minimal inhibition of the other isozymes.

The synthesis of the compounds is described in Davis et al. U.S. Pat. No. 5,057,614, herein incorporated by reference. The novel compounds of Formulas II, III, and IV are readily prepared in an analogous process to that disclosed in U.S. Pat. No. 5,057,614 and known in the art as evidenced by EPO 397 060 (1990) and Bit et al., *J. Med. Chem.* 36: 21-29 (1993). For example, when preparing the novel compounds of Formula II, III, or IV, the alkylation of the indole nitrogen occurs under conditions appreciated in the art. The reaction usually involves approximately equimolar amounts of the two reagents, although other ratios, especially those wherein the alkylating reagent is in excess, are operative. The reaction is best carried out in a polar aprotic solvent employing an alkali metal salt or other such alkylation conditions as are appreciated in the art. When the leaving group is bromo or chloro, a catalytic amount of iodide salt, such as potassium iodide may be added to speed the reaction. Preferred reaction conditions include the following: Potassium hexamethyldisilazide in dimethylformamide or tetrahydrofuran, sodium hydride in dimethylformamide, or cesium carbonate in acetonitrile. The temperature of the reaction is preferably from about ambient temperature to about the reflux temperature of the reaction mixture. When elevated temperatures are employed, the reaction is generally complete in 1-4 hours.

The novel compounds of Formula II, III, and IV can be prepared by procedures described in *Chem. Pharm. Bull.* 33(5) 1826–1835 (1985), *Synth. Commun.*, 18(3) 265–273 (1988) and *J. Org. Chem.*, 44(4) 578–586 (1979) and are generally described in Scheme 1.

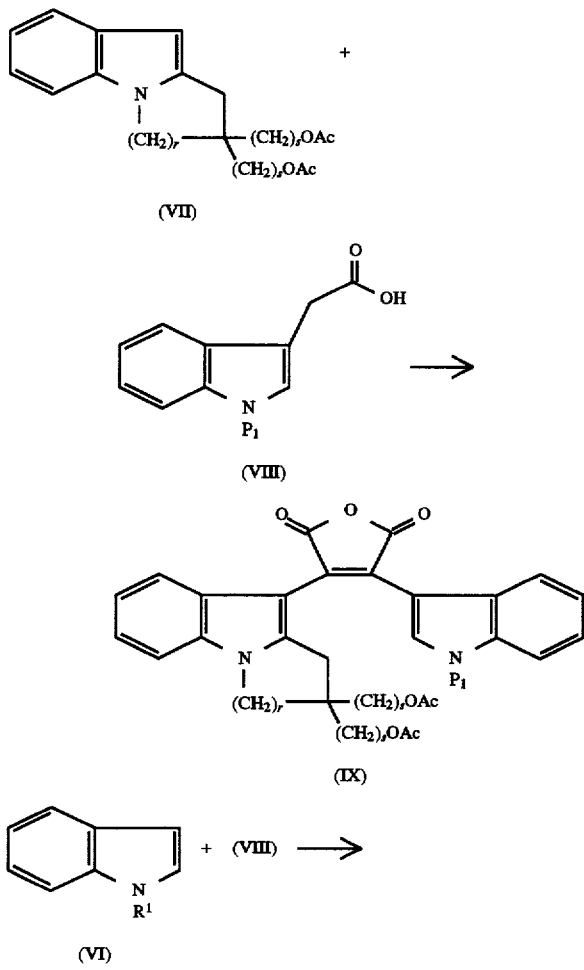

Scheme 1

-continued
Scheme 1

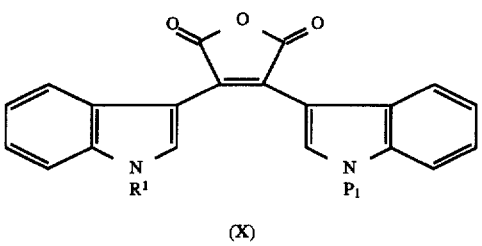

(X)

In the above scheme, r, s, and $R^1$ are the same as previously defined in Formula II, III, or IV; and Ac is acetyl. $P_1$ is a protecting group such as t-butoxycarbonyl or other indole protecting group known in the art. T. W. Greene and P. Wuts, *Protective Groups in Organic Synthesis*, Chapter 7, page 385. The reaction described in Scheme 1 is known as a Perkin Condensation. The reaction is described in Hill et al., *J. Med. Chem.* 36: 21–29 (1993). Generally, oxalyl chloride is added at between −78° C. and the reflux temperature of the mixture (preferably at 0° C.) to an anhydrous solution of Compound VI or VII in inert organic solvent such as a halogenated hydrocarbon like methylene chloride. The volatiles are then removed. The resulting solids are dissolved in a dry halogenated hydrocarbon solvent, e.g. methylene chloride; and added to Compound VIII in the presence of a base, preferably a tertiary amine such as triethylamine, at room temperature.

The acetyloxy alkyl (OAc) of Compound IX may be converted to an alcohol by reacting Compound IX with $NH_4OH$ or aqueous ammonia in DMF at elevated temperatures, e.g. 140° C. The resulting alcohol may be converted to the amine or the other substitutions of Formula III by methods known in the art. For example, the alcohol in dichloromethane and collidine under a nitrogen atmosphere may be reacted with triflic anhydride in dichloromethane. After approximately two hours, the mixture is treated with aqueous ammonia to form the amine.

The conversion of the anhydride of Compound IX or X to the maleimides of Formula I, II, III, or IV occurs by an ammonolysis as described in Brenner et al., *Tetrahedron* 44: 2887–2892 (1988). For example, the anhydride may be converted to the bis-indole maleimide by reacting the anhydride with hexamethyldisilazane and methanol in an inert organic solvent such as DMF at room temperature.

Compounds VI, VII, VIII, and any other reagents required for the reactions described herein, are either commercially available, known in the art, or can be prepared by methods known in the art. For example, Compound VI may be prepared by techniques described in M. Adachi et al., *Chem. Pharm. Bull.*, 33(5), 1826–35 (1985); K. Sasakura et al., *Synth. Commun.*, 18(3), 265–273 (1988).

By virtue of their acidic moieties, the compounds of Formulas II, III, or IV include the pharmaceutically acceptable base addition salts thereof. Such salts include those derived from inorganic bases such as ammonium and alkali and alkaline earth metal hydroxides, carbonates, bicarbonates, and the like, as well as salts derived from basic organic amines such as aliphatic and aromatic amines, aliphatic diamines, hydroxy alkamines, and the like. Such bases useful in preparing the salts of this invention thus include ammonium hydroxide, potassium carbonate, sodium bicarbonate, calcium hydroxide, methylamine, diethylamine, ethylenediamine, cyclohexylamine ethanolamine and the like.

Because of the basic moiety, the compounds of Formulas II, III, or IV can also exist as pharmaceutically acceptable acid addition salts. Acids commonly employed to form such salts include inorganic acids such as hydrochloric, hydrobromic, hydroiodic, sulfuric and phosphoric acid, as well as organic acids such as para-toluenesulfonic, methanesulfonic, oxalic, para-bromophenylsulfonic, carbonic, succinic, citric, benzoic, acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, 2-butyn-1,4 dioate, 3-hexyn-2, 5-dioate, benzoate, chlorobenzoate, hydroxybenzoate, methoxybenzoate, phthalate, xylenesulfonate, phenylacetate, phenylpropionate, phenylbutyrate, citrate, lactate, hippurate, β-hydroxybutyrate, glycollate, maleate, tartrate, methanesulfonate, propanesulfonate, naphthalene-1-sulfonate, naphthalene-2-sulfonate, mandelate and the like salts.

In addition to pharmaceutically-acceptable salts, other salts are included in the invention. They may serve as intermediates in the purification of compounds or in the preparation of other salts, or are useful for the identification, characterization or purification.

The pharmaceutically acceptable salts of compounds of Formulas II, III, or IV can also exist as various solvates, such as with water, methanol, ethanol, dimethylformamide, ethyl acetate and the like. Mixtures of such solvates can also be prepared. The source of such solvate can be from the solvent of crystallization, inherent in the solvent of preparation or crystallization, or adventitious to such solvent. Such solvates are within the scope of the present invention.

It is recognized that various stereoisomeric forms of the compounds of Formulas II, III, or IV may exist; for example, in Formula III, X introduces a chiral carbon atom. The compounds are normally prepared as racemates and can conveniently be used as such, but individual enantiomers can be isolated or synthesized by conventional techniques if so desired. Such racemates and individual enantiomers and mixtures thereof form part of the present invention.

The invention also encompasses the pharmaceutically acceptable prodrugs of the compounds of Formula I, II, III and IV. A prodrug is a drug which has been chemically modified and may be biologically inactive at its site of action, but which may be degraded or modified by one or more enzymatic or other in vivo processes to the parent bioactive form. This prodrug should have a different pharmacokinetic profile than the parent, enabling easier absorption across the mucosal epithelium, better salt formation or solubility, and/or improved systemic stability (an increase in plasma half-life, for example). Typically, such chemical modifications include the following:

1) ester or amide derivatives which may be cleaved by esterases or lipases;
2) peptides which may be recognized by specific or nonspecific proteases; or
3) derivatives that accumulate at a site of action through membrane selection of a prodrug form or a modified prodrug form; or any combination of 1 to 3, supra. Conventional procedures for the selection and preparation of suitable prodrug derivatives are described, for example, in H., Bundgaard, *Design of Prodrugs*, (1985).

As previously noted, the compounds of the present invention are potent, beta-1 and beta-2 isozyme selective PKC inhibitors. As such, they are useful in the treatment of conditions associated with diabetes mellitus and its complications, as well as other disease states associated with an elevation of PKC and, in particular, the beta-1 and beta-2 isozymes.

Protein kinase C beta-1 and beta-2 has been linked to diabetes. Inoguchi et al., *Proc. Natl. Acad. Sci. USA* 89: 11059—11065 (1992). In addition, excessive activity of protein kinase C has been linked to insulin signaling defects and therefore to the insulin resistance seen in Type II diabetes. Karasik, A. et al., *J. Biol. Chem.* 265: 10226–10231 (1990); Chen, K. S. et al., *Trans. Assoc. Am. Physicians* 104: 206–212 (1991); Chin, J. E. et al., *J. Biol. Chem.* 268: 6338–6347 (1993). Further, studies have demonstrated a marked increase in protein kinase C activity in tissues known to be susceptible to diabetic complications when exposed to hyperglycemic conditions. Lee, T.-S. et al., *J. Clin. Invest.* 83: 90–94 (1989; Lee, T.-S. et al., *Proc. Natl. Acad. Sci. USA* 86: 5141–5145 (1989); Craven, P. A. and DeRubertis, F. R. *J. Clin. Invest.* 83: 1667–1675 (1989); Wolf, B. A. et al., *J. Clin. Invest.* 87: 31–38 (1991); Tesfamariam, B. et al., *J. Clin. Invest.* 87: 1643–1648 (1991); Bastyr III, E. J. and Lu, J., *Diabetes* 42: (Suppl 1) 97A (1993).

The novel compounds of the present invention, as an inhibitor of protein kinase C, are useful in the treatment of conditions in which protein kinase C has demonstrated a role in the pathology. Conditions recognized in the art include: diabetes mellitus and its complications, ischemia, inflammation, central nervous system disorders, cardiovascular disease, dermatological disease, Alzheimer's disease, and cancer.

Protein kinase C inhibitors have been shown to block inflammatory responses such as neutrophil oxidative burst, CD3 down-regulation in T-lymphocytes, and phorbol-induced paw edema. Twoemy, B. et al. *Biochem. Biophys. Res. Commun.* 171: 1087–1092 (1990); Mulqueen, M. J. et al. *Agents Actions* 37: 85–89 (1992). Accordingly, as inhibitors of PKC, the present compounds are useful in treating inflammation.

Protein kinase C activity plays a central role in the functioning of the central nervous system. Huang, K. P. *Trends Neurosci.* 12: 425–432 (1989). In addition, protein kinase C inhibitors have been shown to prevent the damage seen in focal and central ischemic brain injury and brain edema. Hara, H. et al. *J. Cereb. Blood Flow Metab.* 10: 646–653 (1990); Shibata, S. et al. *Brain Res.* 594: 290–294 (1992). Recently, protein kinase C has been determined to be implicated in Alzheimer's disease. Shimohama, S. et al., *Neurology* 43: 1407–1413 (1993). Felsenstein, K. M. et al., Negroscience Letters 174: 173–76 (1994). Accordingly, the compounds of the present invention are useful in treating Alzheimer's disease and ischemic brain injury.

Protein kinase C activity has long been associated with cell growth, tumor promotion and cancer. Rotenberg, S. A. and Weinstein, I. B. *Biochem. Mol. Aspects Sel. Cancer* 1: 25–73 (1991). Ahmad et al., *Molecular Pharmacology*, 43: 858–862 (1993). It is known that inhibitors of protein kinase C inhibitors are effective in preventing tumor growth in animals. Meyer, T. et al. *Int. J. Cancer* 43: 851–856 (1989); Akinagaka, S. et al. *Cancer Res.* 51: 4888–4892 (1991). The novel compounds of the present invention also act as multidrug reversal (MDR) agents making them effective compounds when administered in conjunction with other chemotherapeutic agents.

Protein kinase C activity also plays an important role in cardiovascular disease. Increased protein kinase C activity in the vasculature has been shown to cause increased vasoconstriction and hypertension. A known protein kinase C inhibitor prevented this increase. Bilder, G. E. et al. *J. Pharmacol. Exp. Ther.* 252: 526–530 (1990). Because protein kinase C inhibitors demonstrate inhibition of the neutrophil oxidative burst, protein kinase C inhibitors are also useful in treating cardiovascular ischemia and improving cardiac function following ischemia. Muid, R. E. et al. *FEBS Lett.* 293: 169–172 (1990); Sonoki, H. et al. *Kokyu-To Junkan* 37: 669–674 (1989). The role of protein kinase C in platelet function has also been investigated and as shown elevated protein kinase C levels being correlated with increased response to agonists. Bastyr III, E. J. and Lu, J. *Diabetes* 42: (Suppl. 1) 97A (1993). PKC has been implicated in the biochemical pathway in the platelet-activity factor modulation of microvascular permeability. Kobayashi et al., *Amer. Phys. Soc.* H1214–H120 (1994). Potent protein kinase C inhibitors have been demonstrated to affect agonist-induced aggregation in platelets. Toullec, D. et al. *J. Biol. Chem.* 266: 15771–15781 (1991). Protein kinase C inhibitors also block agonist-induced smooth muscle cell proliferation. Matsumoto, H. and Sasaki, Y. *Biochem. Biophys. Res. Commun.* 158: 105–109 (1989). Therefore, the present novel compounds are useful in treating cardiovascular diseases, atherosclerosis and in particular, restenosis.

Abnormal activity of protein kinase C has also been linked to dermatological disorders such as psoriasis. Horn, F. et al. *J. Invest. Dermatol.* 88: 220–222 (1987); Raynaud, F. and Evain-Brion, D. *Br. J. Dermatol.* 124: 542–546 (1991). Psoriasis is characterized by abnormal proliferation of keratinocytes. Known protein kinase C inhibitors have been shown to inhibit keratinocyte proliferation in a manner that parallels their potency as PKC inhibitors. Hegemann, L. et al. *Arch. Dermatol. Res.* 283: 456–460 (1991); Bollag, W. B. et al. *J. Invest. Dermatol.* 100: 240–246 (1993). Accordingly, the novel compounds as inhibitors of PKC are useful in treating psoriasis.

The ability of the compounds of the present invention to selectively inhibit protein kinase C beta-1 and beta-2 isozyme was determined in the PKC Enzyme assay.

PKC Enzyme Assay

PKC enzymes=alpha, beta I, beta II, gamma, delta, epsilon, eta and zeta.

Assay components in a total volume of 250 µL are the following: Vesicles consisting of 120 µg/mL phosphatidylserine (Avanti Polar Lipids) and sufficient diacylglycerol (Avanti Polar Lipids) to activate the enzyme to maximum activity in 20 mM HEPES buffer (Sigma, St. Louis, Mo.), pH 7.5, 940 µM calcium chloride (Sigma, St. Louis, Mo.) for assaying the alpha, beta I, beta II and gamma enzyme only, 1 mM EGTA for all the enzymes, 10 mM magnesium chloride (Sigma, St. Louis, Mo.) and 30 µM (gamma-32P) ATP (DuPont). For all the enzymes either histone type HL (Worthington) or myelin basic protein is used as substrate. The assay is started by addition of protein kinase C enzyme incubated at 30° C. for 10 minutes and stopped by adding 0.5 mL of cold trichloroacetic acid (Amresco) followed by 100 µL of 1 mg/mL bovine serum albumin (Sigma, St. Louis, Mo.). The precipitate is collected by vacuum filtration on glass fiber filters employing a TOMTEC™ filtration system and quantified by counting in a beta scintillation counter.

Using the methodology described, representative compounds were evaluated and were found to have an IC$_{50}$ value with respect to the beta-1 and beta-2 isozyme of below 10 µm. Surprisingly, the compounds are isozyme selective, i.e., the compounds preferentially inhibit protein kinase C beta-1 and beta-2 isozyme over the protein kinase C isozymes, alpha, gamma, delta, epsilon, zeta, and eta. In general, the compounds demonstrate a minimum of a ten fold differential in the dosage required to inhibit PKC beta-1 or beta-2 isozyme and the dosage required for equal inhibition of the alpha protein kinase C isozyme as measured in this assay. Therefore, as selective inhibitors of PKC isozyme beta-1 and beta-2, the compounds are useful in the treatment of conditions in which PKC beta isozymes have demonstrated a role in the pathology, in particular, diabetes mellitus and its complications.

The following examples and preparations are provided merely to further illustrate the invention. The scope of the invention is not construed as merely consisting of the following examples. In the following examples and preparations, melting point, nuclear magnetic resonance spectra, mass spectra, high pressure liquid chromatography over silica gel, N,N-dimethylformamide, palladium on charcoal, diisobutylaluminum hydride, acetonitrile, and tetrahydrofuran are abbreviated M.Pt., NMR, MS, HPLC, DMF, Pd/C, DIBAL, ACN and THF, respectively. The terms "NMR" and "MS" indicate that the spectrum was consistent with the desired structure. The term "ND" indicates that data are not available.

Preparation 1

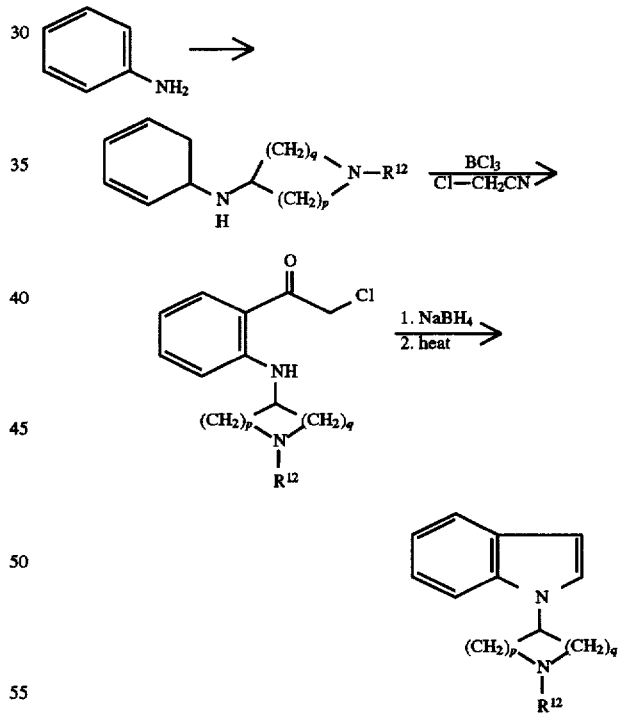

The above reaction is carried out in a manner analogous to M. Adachi et al., *Chem. Pharm. Bull.*, 33(5), 1826–35 (1985); and K. Sasakura et al., *Synth. Commun.*, 18(3), 265–273 (1988).

Preparation 2

2-(1-(1-N(H)-piperidin-4-yl)-indol-3-yl)-acetic acid ethyl ester

To a solution of 4-(1-indolyl)-piperidine (300 mg, 1.5 mmol) was added dry ethanol (3 mL) and anhydrous potassium carbonate (410 mg, 3 mmol). After 20 minutes, ethyl bromoacetate (0.17 mL, 1.5 mmol) was added. After 12 hours, the reaction was quenched with water, extracted with ethyl acetate (3×), washed with water, dried, and concentrated to a residue. The residue was eluted through a column of silica gel with toluene/acetone (80:20). Evaporation of the eluding solvent gave of the title compound (300 mg) as a brownish oil (70% of theory).

Preparation 3

1-(1-Ethyl-piperidin-4-yl)-1H-indole

To a solution of 1-piperidin-4-yl-1H-indole (0.6 g, 3 mmol) in 5 mL of dry ethanol was added anhydrous potassium carbonate (680 mg, 4.9 mmol). After stirring for 15 minutes at ambient temperature, ethyl p-toluenesulfonate (0.48 mL, 4.5 mmol) was added. The reaction was heated under reflux for 24 hours with stirring, quenched with water, extracted with methylene chloride (2×), dried and evaporated to give a residue. The residue was chromatographed on silica gel with toluene/acetone (50:50) to yield 360 mg straw colored material (53% of theory).

Preparation 4

1-[(1-N-Cyclopropylmethyl)-piperidine-4-yl]-indole

To a solution of 4-(1-indolyl)-piperidine (0.6 g, 3 mmol) in dry ethanol (4 mL) was added anhydrous potassium carbonate (680 mg, 4.9 mmol). After 15 minutes, bromomethylcyclopropane (0.29 mL, 4.5 mmol) was added and stirring was continued over night. Additional potassium carbonate (0.22 g) and bromomethylcyclopropane (0.14 mL) was added. After 3 hours, the reaction mixture was quenched with water and extracted with ethyl acetate (3×). The combined organic phases were washed with water, dried, evaporated, and purified by column chromatography on silica gel eluting with methylene chloride/ethanol (98:2). Evaporation of the eluting solvent gave the title compound. 480 mg (63% yield).

Preparation 5

1-N-[1-N-(3-chloropropyl)-piperidin-4-yl]-indole

To a solution of 1-(piperidin-4-yl)-indole (100 mg, 0.5 mmol) in absolute ethanol (2 mL) was added anhydrous potassium carbonate (70 mg, 0.5 mmol) and 1-bromo-3-chloropropane (150 mg, 1 mmol). After stirring overnight additional 1-bromo-3-chloropropane (150 mg) was added and stirring continued for 2 hours. The mixture was evaporated; and the residue dissolved in methylene chloride and shaken with water. The organic solution was dried over anhydrous potassium carbonate and evaporated. The residue was chromatographed on silica gel with methylene chloride/ethanol (95:5) to give the title compound (90 mg, 65% yield).

Preparation 6

[3-(4-Indol-1-yl-piperidin-1-yl)-propyl]-dimethylamine

A mixture of 1-N-[1-N-(3-chloro-propyl)-piperidin-4-yl] -indole (900 mg, 3.25 mmol), anhydrous potassium carbonate (440 mg, 3.25 mmol) and dimethylammonium hydrochloride (260 mg, 3.25 mmol) in absolute ethanol (10 mL) was refluxed for 6 hours, evaporated and suspended in water. The mixture was extracted with methylene chloride, dried over anhydrous potassium carbonate, and evaporated to yield 1 g of the desired compound (100% of theory).

Preparation 7

1-Benzyl-4-(1-indolyl)-piperidine

This compound was prepared in a manner analogous to the synthesis described in the literature: a) M. Adachi et al., Chem. Pharm. Bull., 33(5), 1826–35 (1985); b) K. Sasakura et al., Synth. Commun., 18(3), 265–273 (1988).

Preparation 8

1-t-butoxycarbonyl-4-(1-indolyl)-piperidine

To a 0° C. methylene chloride (20 mL) solution of tert-butoxycarbonate (5.44 mmol) containing triethylamine (0.76 mL, 5.44 mmol) was added 4-(1-indolyl)-piperidine (1.09 g, 5.44 mmol). The reaction was brought to room temperature. After 4 hours, the reaction was quenched with sat NaHCO$_3$, water (2×), dried, filtered and concentrated. The residue was purified by flash chromatography eluting with methylene chloride to give the title compound 1.25 g (76% yield) as an oil which crystallized on standing.

Preparation 9

4-(1-indolyl)-piperidine

A glacial acetic acid (15 mL) solution containing Pd(OH)$_2$/C and 1-benzyl-4-(1-indolyl)-piperidine was placed under an H$_2$ atmosphere. The reaction temperature was raised to 80° C. After 1 hour, the reaction was cooled to room temperature and filtered. The filtrate was made basic (pH 8–9) with saturated NaHCO$_3$, and extracted with methylene chloride. The extract was washed with water, dried, and concentrated. This material was sufficiently pure for further reactions giving 1.09 g (80% yield) of the title compound.

Preparation 10

6,7,8,9-tetrahydropyrido[1,2-a]indole-8,8-dicarboxylic acid diethyl ester

To a −78° C. THF (12 mL) solution of lithium diisopropylamide (generated in situ from diisopropylamine (3.8 mL) and 15% n-butyl lithium in hexane (17 mL) at 0° C.) was added dropwise a THF solution of 6,7,8,9-tetrahydropyrido [1,2-a]indole-8-carboxylic acid ethyl ester. After 30 minutes, the temperature was brought to 0° C. After 1 hour, ethyl chloroformate (2.6 mL) was added over one hour. The reaction was allowed to come to room temperature overnight. The reaction was quenched with saturated NH$_4$Cl and extracted t-butyl methyl ether (3×). The extract was washed with water, dried, filtered, and concentrated to give a residue. The residue was purified by flash chromatography eluting with 15% ethyl acetate/hexane to give the title compound 1.29 g (33% yield) as off white crystals (M.Pt. 69° C.).

Preparation 11

1-(1-Methyl-piperidin-4-yl)-indole

To an ice cooled solution of 4-indol-1-yl-piperidine-1-carboxylic acid ethyl ester (50 g, 0.18 mol) in dry THF (400 mL) was added LAH in small portions (7 g, 0.18 mol). After 2 hours, the mixture was quenched by successive addition of water (7 mL) 15% of sodium hydroxide (7 mL) and water (21 mL). The reaction mixture was filtered. The filtrate was dried and evaporated. The residue crystallized on standing and was recrystallized from a small amount of di-i-propyl ether to give the title compound (25 g, 63% of theory). M.Pt.: 58° C.

Preparation 12

4-(Indol-1-yl)-piperidine-1-carboxylic acid ethyl ester

To a solution of 1-N-(1-benzyl-piperidin-4-yl)-indole (100 g, 0.344 mol) in methylene chloride (1 L) was added ethyl chloroformate (99.2 mL) dropwise with stirring. The mixture was refluxed for 48 hours, cooled to room temperature, and concentrated. The residue was crystallized from i-propanol to give the title compound as colorless crystals (50 g, 53% yield). M.Pt.: 127° C.

Preparation 13

1-N-(1-N-(Cyclopropylmethyl)-piperidin-4-yl)-indole

To a solution of 1-N-(piperidin-4-yl)-indole (0.6 g, 3 mmol) in dry ethanol (4 mL) was added anhydrous potassium carbonate (680 mg, 4.9 mmol). After stirring for 15 minutes at ambient temperature, bromomethylcyclopropane (0.29 mL, 4.5 mmol) was added. Stirring was continued overnight. An additional amount of carbonate (0.22 g) and bromomethylcyclopropane (0.14 mL) was added. After 3 hours, the reaction mixture was quenched with water and extracted with ethyl acetate (3×). The combined organic phase was washed with water, dried, evaporated, and purified by column chromatography on silica gel eluting with methylene chloride/ethanol (98:2). Evaporation of the eluting solvent gave the title compound as an oil (480 mg, 63% yield).

Preparation 14

1-N (1-N-i-Propyl-piperidin-4-yl)-1H-indole

To a solution of 1-(piperidin-4-yl)-indole (0.5 g, 2.5 mmol) in dry DMF (3 m) was added anhydrous potassium carbonate (360 mg, 2.6 mmol). After stirring for 15 minutes at ambient temperature, i-propyl bromide (0.84 mL, 9 mmol) was added. The reaction mixture was refluxed for 2 days with stirring, quenched with water, extracted with ethyl acetate (2×), dried, and evaporated. The remaining residue was chromatographed on silica gel eluting with a toluene/acetone gradient (90:10 to 70:30). Evaporation of the eluting solvent gave the title compound as an oil. (220 mg, 36% yield).

Preparation 15

1-N-[1-N-(2,2,2-Trifluoro-ethyl)-piperidin-4-yl]-indole

To a solution of 1-N-(1-N-(trifluoroaceto)piperidin-4-yl)-indole (400 mg, 1.35 mmol) in dry THF (3 mL) was added dropwise a 10N solution of borate methyl sulfide (0.15 mL) complex. The mixture was stirred at 60° C. for 3 hours, cooled, quenched with 2N aqueous sodium hydroxide, and brought to pH 10. The mixture was diluted with water and extracted with t-butyl methyl ether (2×). The combined organic solutions were washed with water (2×), dried, and evaporated. The residue solidified on standing and was recrystallized from hexane to give the title compound as colorless crystals (190 mg, 50% yield). M.Pt.: 79°–81° C.

Preparation 16

1-N-(1-N-(trifluoroacetyl)piperidin-4-yl)-indole

To an ice cooled solution of 1-N-(piperidin-4-yl)-indole (1.0 g, 5 mmol) in dry pyridine (5 mL) was carefully added trifluoroacetic acid anhydride (0.71 mL, 5 mmol). After stirring for 48 hours at ambient temperature, all volatiles were evaporated. The residue was redissolved and evaporated with toluene (×2). The residue was taken up in water and extracted twice with t-butyl methyl ether. The combined organic phase was washed with water, dried, and evaporated. The residue was triturated with ether. The crystalline precipitate formed was separated and discarded. After evaporation of the filtrate, the residue was purified by column chromatography on silica gel eluting with toluene/acetone 98:2 to give 410 mg of off white crystals (28% of theory). M.Pt.: 130°–132° C.

Preparation 17

1-N-[1-N-(2,2,3,3,4,4,4-Heptafluoro-butyl)-piperidin-4-yl]-indole

To a solution of 1-N-[(1-N-2,2,3,3,4,4,4-heptafluoro) butyramido-piperidin-4-yl]-indole (750 mg, 1.89 mmol) in 5 mL of absolute THF was added dropwise a 10N solution of borane methyl sulfide (0.19 mL) complex. The mixture was stirred at 60° C. for 3 hours. After cooling, the mixture was decomposed with 2N aqueous sodium hydroxide and brought to pH 10, diluted with water and extracted with t-butyl methyl ether twice. The combined organic solutions were washed with water twice, dried, and evaporated. The residue was chromatographed on silica gel with toluene as the eluant. The eluant was evaporated to give 430 mg of a yellowish oil (60 % of theory).

Preparation 18

1-N-[(1-N-2,2,3,3,4,4,4-heptafluoro)butyramido-piperidin-4-yl]-indole

To an ice cooled solution of 1-N-(piperidin-4-yl)-indole (1.0 g, 5 mmol) in dry pyridine (3 mL) was carefully added heptafluorobutyric acid chloride (0.75 mL, 5 mmol). After stirring for 16 hours at ambient temperature, the mixture was quenched with water and extracted with ethyl acetate (3×). The combined organic phase was washed with water, dried, and evaporated. The residue was purified by column chromatography on silica gel eluting with toluene/acetone 97:3 to give 1.34 g of brownish oil (68% of theory).

Preparation 19

[t-Butoxycarbonylimino-(4-indol-1-yl-piperidin-1-yl)-methyl]-carbamic acid t-butyl ester This material was prepared by the known procedure. *Tetrahedron Letters* 1993, 34(48), 7677. To an ice cooled solution of 1-piperidin-4-yl-1H-indole (0.6 g, 3 mmol), N,N-bis-t-butoxycarbonylthiourea (0.83 g, 3 mmol) and triethylamine (1.38 g, 9.9 mmol) in dry DMF (5 mL) was carefully added copper(II) chloride dihydrate (exothermic) (0.56 g, 3.3 mmol). After stirring for 30 minutes at ambient temperature, the mixture was diluted with ethyl acetate and filtered over Hyflo. The filtrate was washed twice each with brine and water, dried, evaporated. The residue was purified by column chromatography on silica gel eluting with toluene/acetone 95:5. 0.61 g of yellow crystals (46% of theory). M.Pt.: 115°–118° C.

Preparation 20

1-N-(1-Methyl-piperidin-4-yl)methylene)-indole

To an ice cooled stirred suspension of lithium aluminum hydride (LAH) (85 mg, 2.24 mmol) in absolute THF (7 mL) was added 4-(indol-1-yl)methylenepiperidine-1-carboxylic acid ethyl ester (0.64 g, 2.23 mmol) in 4 mL of absolute THF and then stirred at ambient temperature. After 2 hours, additional LAH (85 mg, 2.24 mmol) was added and stirring continued for 1 hour. The mixture was cooled to 0° C. and quenched by successive addition of water (0.17 mL), 15% aqueous sodium hydroxide (0.17 mL), water (0.51 mL), stirred for 30 minutes, filtered, and evaporated to dryness. The residue was taken up in water (40 mL) and extracted (2×) with t-butyl methyl ether (30 mL). The combined organic phases were washed with water (2×), dried, and evaporated. The remaining oily residue was sufficiently pure for further reaction.

Preparation 21

4-(Indol-1-yl)methylene-piperidine-1-carboxylic acid ethyl ester

To a stirred solution of indole (0.53 g, 4.5 mmol) in dry DMF (15 mL) was added potassium t-butoxide (580 mg, 5.2 mmol) at ambient temperature. After stirring for 30 minutes, 4-(methanesulfonyloxymethylene)-piperidine-1-carboxylic acid ethyl ester (1.2 g, 4.5 mmol) was added. After 8 hours, the reaction mixture was quenched with water and extracted with t-butyl methyl ether (2×50 mL). The combined organic phases were washed with water (2×), dried, evaporated, and purified by column chromatography on silica gel eluting with toluene/acetone 96:4. Evaporation of the eluting solvent gave 0.92 g (71% of theory) of a slightly bluish oil.

Preparation 22

2-(Indol-1-yl)butyrolactone

An ice cooled solution of indole (9 g, 78 mmol) in dry THF (80 mL) was treated with oil free sodium hydride (2.25 g, 94 mmol). After 1 hour, a solution of 2-bromobutyrolactone (14.6 mL, 78 mmol) in dry THF (20 mL) was added dropwise. After stirring overnight at ambient temperature, the mixture was poured on crushed ice, extracted with ethyl acetate (3×), dried, and evaporated. The residue was purified by flash chromatography on silica gel with a hexane/ethyl acetate gradient (9:1 to 7:3). Evaporation of the eluting solvent gave 8 g of a yellowish oil (52% of theory).

Preparation 23

2-(Indol-1-yl)-butane-1,4-diol

To an ice cooled suspension of LAH (0.84 g, 0.022 mol) in dry THF (60 mL) was added 2-(indol-1-yl)butyrolactone (4 g, 0.02 mol). After 1 hour the mixture was quenched successively with water (0.84 mL), 15% aqueous sodium hydroxide (0.84 mL), and water (2.5 mL). The reaction was filtered and the filtrate was dried, and evaporated. The material obtained, 2.5 g of colorless oil (61% of theory), was used directly in the next reaction.

Preparation 24

1,4-(Bis)methanesulfonyloxy-2-(indol-1-yl)-butane

An ice cooled solution of 2-(indol-1-yl)-butane-1,4-diol (2 g, 10 mmol) containing triethylamine (3.6 mL, 26 mmol) in dry methylene chloride (30 mL) was treated with methanesulfonyl chloride (1.86 mL, 12 mmol). After stirring over night, the mixture was poured onto crushed ice, extracted with methylene chloride (3×), dried, and evaporated. The crude material, 2.5 g (71% of theory) was used in the next reaction.

Preparation 25

1,4-Diiodo-2-indol-1-yl-butane

An acetone solution (20 mL) containing 1,4-(bis) methanesulfonyloxy-2-(indol-1-yl)-butane (0.5 g, 1.4 mmol) and sodium iodide (1.86 g, 12.5 mmol) was refluxed for 4 hours, cooled, and filtered. The filtrate was evaporated. The residue, 400 mg (70% of theory), was used directly in the next reaction.

Preparation 26

1-N-(1-Benzyl-pyrrolidin-3-yl)-indole

To a solution of 1,4-diodo-(2-indol-1-yl)-butane (400 mg, 0.94 mmol) in THF (20 mL) was added successively benzyl amine (0.12 mL, 1.07 mmol) and triethyl amine (0.15 mL, 2.9 mmol). The mixture was refluxed for 1 hour and evaporated. The residue was dissolved in t-butyl methyl ether. The organic solution was washed with water (2×), dried, and evaporated. The oily residue was purified by HPLC on silica gel using methylene chloride/ethanol (98:2). Evaporation of the eluting solvent gave 110 mg of a pale oil (42% of theory).

Preparation 27

1-N-(1-Benzhydryl-azetidin-3-yl)-indole

A solution of 2-[2-(1-(benzhydryl)-azetidin-3-yl)-2-amino)-phenyl]-ethanol (3.1 g, 0.01 mol) in dry methylene chloride (100 mL) was cooled to −5° C. and treated with pyridinium dichromate (PDC) (9.3 g) in small portions. The mixture was slowly brought to ambient temperature and additional PDC (9.3 g) was added. After 1 hour, the mixture was filtered through a layer of dry silica gel, rinsed with methylene chloride diethyl ether after evaporation of the eluant. (0.85 g) a yellow oil, which was used without further purification. (25% of theory). MS

Preparation 28

1-N-(1-N-(benzhydryl)-azetidin-3-yl)-2-(ethan-2-ol)-analine

A mixture of methanesulfonic acid 1-benzhydryl-azetidin-3-yl ester (14 g, 44.2 mmol), 2-(ethan-2-ol)-analine (14 g, 44.2 mmol), and anhydrous potassium carbonate (2.8 g, 50 mmol) in dry toluene (150 mL) was refluxed for 4 hours. The toluene was evaporated, and the residue was partitioned between water and methylene chloride. The organic phase was dried, evaporated, and the remaining oil was purified by column chromatography on silica gel eluting with a hexane/acetone gradient (90:10 to 85:15). Evaporation of the eluting solvent gave 6 g of a colorless oil (44% of theory). MS

Preparation 29

Methanesulfonic acid 1-benzhydryl-azetidin-3-yl ester

A solution of 1-benzhydryl-azetidin-3-ol (50 g, 0.208 mol) in dry pyridine (500 mL) was cooled to 5° C. Methane sulfonyl chloride (16.2 mL, 0.208 mol) was added over 30 minutes. The mixture was slowly (12 hours) brought to ambient temperature and stirring was continued for additional 2 hours. The solvent was removed in vacuo at 40° to 50° C. The residue was redissolved in methylene chloride, washed with water (2×), and dried. The crude material was triturated with a solution of t-butylmethylether/petroleum ether (15:85), to produce the purified product as crystals. (53 g, 80% yield). M.Pt.: 85°–87° C. MS

Preparation 30

Methyl-2-deoxy-5-O-tosyl-D-ribose

Methyl-2-deoxy-D-ribose (8 g, 54 mmol) was dissolved in pyridine (60 mL). To this solution was added tosylchloride (10.86 g, 57 mmol) over 1 hour at 0° C. After 14 hours at room temperature, the solution was concentrated, quenched with ice water (250 mL), and extracted with ethyl acetate. The extract was washed with saturated NaHCO$_3$, water, dried, filtered, and concentrated. The residue (13.6 g, 83.5% yield) was used directly. NMR

Preparation 31

Methyl-5-azido-2,5 dideoxy-D-ribose

To a solution of methyl-2-deoxy-5-O-tosyl-D-ribose (13.6 g, 45 mmol) in DMF (250 mL) was added sodium azide (4.4 g, 67 mmol). The mixture was refluxed for 4 hours, cooled to room temperature, quenched with ice water (1.5 mL), and extracted with ethyl-acetate. The extract was washed with water, dried, and concentrated to give an oil (6.2 g, 86% yield). NMR

Preparation 32

Methyl-3-O-acetyl-5-azido-2,5-dideoxy-7-D-ribose

Acetic anhydride (25 mL) was added to a solution of methyl-5-azido-2.5-dideoxy-D-ribose (6.2 g, 38 mmol) in pyridine (100 mL). After 4 hours at room temperature, the mixture was concentrated in vacuo. The residue (6 g) was purified by flash chromatography eluting with hexanethylacetate (8:2). Evaporation of the eluting solvent gave the product as an oil (4.9 g, 60% yield). NMR

Preparation 33

3-O-Acetyl-5-azido-2,5-dideoxy-D-ribosylacetate

To a 25° C. cooled solution of methyl-3-O-acetyl-5-azido-2,5-dideoxy-D-ribose (2.5 g, 11.6 mmol) in acetic anhydride (30 mL) was added acetic anhydride containing trace sulfuric acid (26 mL, 50:1). After 45 minutes, the mixture was diluted with methylene chloride (300 mL), quenched with saturated NaHCO$_3$, washed with water, dried, filtered and concentrated. The residue was purified by flash chromatography eluting with hexan-ethylacetate (8:2).

Preparation 34

8,8-bis(acetoxymethylene)-6,7,8,9-tetrahydropyrido [1,2-a]indole

To a toluene (4 mL) solution of 8,8'-bis (acetoxymethylene)-6,7,8,9-tetrahydropyrido[1,2-a]indole-8,8'-dicarboxylic acid diethyl ester (1.2 g, 3.8 mmol) was added a hexane solution of 1M diisobutylaluminum hydride. After 1 hour, acetic anhydride (15 mL) was added. After an additional 15 hours, 4-dimethylaminopyridine (100 mg) was added, and the reaction temperature brought to 65° C. for 3 hours. The reaction was filtered, washing with t-butylmethyl ether. The filtrate was washed with water, dilute aqueous HCl, saturated NaHCO$_3$, and water. Evaporation of the solvents gave a residue that was purified by chromatography eluting with 60% hexane/acetone to give the title compound in 42% yield.

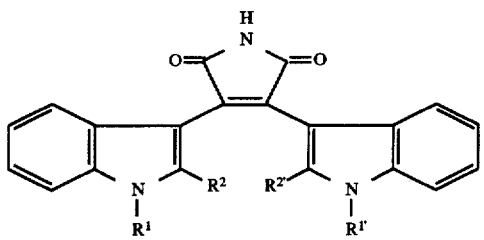

EXAMPLE 1

3-[8,8-bis(acetoxymethylene)-6,7,8,9-tetrahydropyrido[1,2-a]indol-10-yl]-4-(1-methyl-3-indolyl)-1H-pyrrole-2,5-dione To a 0° C. methylene chloride (2.5 mL) solution of 8,8'-bis(acetoxymethylene)-6,7,8,9-tetrahydropyrido[1,2-a] indol (220 mg, 0.7 mmol) was added oxalyl chloride (0.067 mL, 0.84 mmol). The reaction temperature was raised to room temperature for 15 minutes and concentrated in vacuo. To a 0° C. toluene (5 mL) solution of the concentrate containing isopropyl(1-methyl)indol-3-yl)acetimidate hydrochloride was added dropwise triethylamine (0.4 mL, 0.028 mmol). The reaction was warmed to room temperature. After 1 hour, the reaction was poured into 1% aqueous HCl (50 mL), extracted with toluene, dried, and filtered. The filtrate was treated with p-toluene sulfonic acid hydrate (260 mg, 14 mmol). After 1 hour, the filtrate was washed with water, saturated NaHCO$_3$, dried, filtered, and concentrated to give a residue. The residue was recrystallized from t-butyl ether/hexane to give the title compound 150 mg (40% yield) as red crystals (M.Pt. 245° C.).

Alternatively, the compound is prepared in a manner analogous the methods described in EPA 0 384 349, *Tetrahedron Lett.*, 31(16) 2353–2356 (1990) and Tetrahedron Lett., 31(36) 5201–5204 (1990).

| | | IC$_{50}$ (μm) | | | | | | | |
|---|---|---|---|---|---|---|---|---|---|
| Example 1 | | α | β1 | β2 | γ | δ | ε | ζ | η |
| R$^1$R$^2$ | —CH$_2$CH$_2$CR$^8$R$^9$CH$_2$— | 9.8 | 0.36 | 0.3 | 38 | 47 | 150 | 50 | 121 |
| R$^8$ | —CH$_2$OCOCH$_3$ | | | | | | | | |
| R$^9$ | —CH$_2$OCOCH$_3$ | | | | | | | | |

| Example 1 | α | β1 | β2 | γ | δ | ε | ζ | η |
|---|---|---|---|---|---|---|---|---|
| | | | | IC$_{50}$ (μm) | | | | |
| R$^{1'}$ CH$_3$ | | | | | | | | |
| R$^{2'}$ H | | | | | | | | |

EXAMPLE 2

3-[8,8-bis(hydroxymethylene)-6,7,8,9-tetrahydropyrido[1,2-a]indol-10-yl]-4-(1-methyl-3-indolyl)-1H-pyrrole-2,5-dione To an ethanol (3 mL) solution of sodium ethoxide (0.4 mmol) was added 3-[8,8'-bis(acetoxymethylene)-6,7,8,9-tetrahydropyrido[1,2-a]indol-10-yl]-4-(1-methyl-3-indolyl)-1H-pyrrole-2,5-dione (80 mg, 0.15 mmol). After 2 hours, the reaction was acidified with acetic acid to pH 4, diluted with water (10 mL) and extracted with methylene chloride. Evaporation of the organic phase gave the title compound 60 mg (89% yield) as red crystals (M.Pt. 242°–244° C.).

EXAMPLE 4

3-(1-[4-(1-benzyl)-piperidinyl]-3-indolyl)-4-(1-methyl-3-indolyl)-1H-pyrrole-2,5-dione To a 0° C. methylene chloride (2.5 mL) solution of 1-benzyl-4-(1-indolyl)piperidine (290 mg, 1 mmol) was added oxalyl chloride (0.10 mL). The reaction was brought to room temperature. After 30 minutes, the volatiles were removed in vacuo below 30° C. The residue was dissolved in methylene chloride (25 mL) and added dropwise to a methylene chloride (20 mL) solution of isopropyl(1-methyl)indol-3-yl)acetimidate hydrochloride (270 mg, 1 mmol) containing triethylamine (4 mmol) and 4 Å molecular sieves

| Example 2 | α | β1 | β2 | γ | δ | ε | ζ | η |
|---|---|---|---|---|---|---|---|---|
| | | | | IC$_{50}$ (μm) | | | | |
| R$^1$R$^2$ —CH$_2$CH$_2$CR$^8$R$^9$CH$_2$— | 3.5 | 0.070 | 0.060 | 8.8 | 6.8 | 31.8 | 33 | 5.7 |
| R$^8$ —CH$_2$OH | | | | | | | | |
| R$^9$ —CH$_2$OH | | | | | | | | |
| R$^{1'}$ CH$_3$ | | | | | | | | |
| R$^{2'}$ H | | | | | | | | |

EXAMPLE 3

3-(1-[2-(5-Acetamido-2,5-dideoxy-α-D-ribopyranosyl)-hydroxyethyl]-3-indolyl)-4-(1-methyl-3-indolyl)-1H-pyrrole-2,5-dione The titled compound was prepared in a manner analogous to Example 37. α anomer: $^1$H-NMR (CDCl$_3$): 1.9 (3H, s, NAc), 2.2 (2H, m, H-2ab), 3.8 (2H, m, CH$_2$), 3.85 (3H, s, NCH$_3$), 4.2 (2H, m, CH$_2$), 5.05 (1H, d, H-1), 6.7–7.8 (10H, indole H), 8.4 (1H, s, NH)

(2.8 g). After 18 hours, p-toluene sulfonic acid (950 mg, 5 mmol) was added. After 2 hours, the reaction was filtered. The filtrate washed with saturated NaHCO$_3$, water (2×), dried, filtered, and concentrated. The concentrate was purified by flash chromatography eluting with 10% acetone/toluene to give the title compound 50 mg (10% yield) as red crystals. MS. 1H-NMR (CDCl3, 250 MHz) δ 2.02–2.26 (6H, m), 3.06 (2H, m), 3.64 (2H, s), 3.84 (3H, 2), 4.24 (1H, m), 6.68 (1H, m), 6.81 (2H, m), 7.11 (3H, m), 7.28 (7H, m), 7.69 (1H, s), 7.85 (1H, s), 8.50 (1H, bs). MS 515 [M$^+$+H], calculated. 514 FW.

| Example 3 | α | β1 | β2 | γ | δ | ε | ζ | η |
|---|---|---|---|---|---|---|---|---|
| | | | | IC$_{50}$ (μm) | | | | |
| R$^1$ | 0.32 | 0.036 | 0.025 | 4.4 | 0.41 | 0.60 | 46 | 1.1 |

[structure: α-L ribopyranosyl with AcNH, HO substituents]

| R$^2$ | H |
| R$^{1'}$ | CH$_3$ |
| R$^{2'}$ | H |

| Example 4 | IC$_{50}$ (μm) | | | | | | | |
|---|---|---|---|---|---|---|---|---|
| | α | β1 | β2 | γ | δ | ε | ζ | η |
| | 6 | 0.05 | 0.03 | 7 | 6 | 4 | >100 | 0.5 |

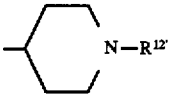

R$^1$
R$^2$ H
R$^{1'}$ CH$_3$
R$^{2'}$ H
R$^{12'}$ benzyl

EXAMPLE 5

To a stirred 0° C. solution of [t-butoxycarbonylimino-(4-indol-1-yl-piperidin-1-yl)-methyl]-carbamic acid t-butyl ester (0.85 g, 1.92 mmol) in dry methylene chloride (5 mL) was added oxalyl chloride (0.18 mL, 2.11 mmol). After 30 minutes at room temperature, the reaction mixture was concentrated below 30° C., dissolved in dry methylene chloride (10 mL), and treated with isopropyl(1-methyl)indol-3-yl)acetimidate hydrochloride (0.54 g, 2.02 mmol). Triethylamine (0.54 g, 2.02 mmol) was added at 0° C. The mixture was stirred at ambient temperature for 3 hours. p-Toluene sulfonic acid monohydrate (1.8 g, 9.6 mmol) was added to the reaction. After 30 minutes, the reaction was quenched with saturated Na$_2$CO$_3$ (40 mL). The organic phase was separated, washed with Na$_2$CO$_3$ (sat. aq.), brine, water, dried, and evaporated. The residue was purified by column chromatography on silica gel eluting with toluene/acetone (9:1). Evaporation of the eluting solvent gave a residue. The residue was recrystallized from diisopropyl ether (150 mg), work up of the mother liquor yielded a second crop (60 mg). Overall yield: 210 mg of bright orange crystals (16% of theory). M.Pt.: 238°–245° C. 1H-NMR (CDCl3, 250 MHz) δ 1.49 (18H, s), 2.02 (2H, m), 2.02 (4H, m), 3.09 (2H, m), 3.86 (3H, s), 5.29 (3H, m), 6.66 (2H, m), 6.91 (1H, m), 7.16–7.36 (5H, m), 7.48 (1H, s), 7.75 (1H, s), 10.18 (1H, bs). MS 667 [M$^+$+H], calculated. 666 FW.

dissolved in methylene chloride (5 mL). This solution was added dropwise to a 0° C. methylene chloride (3 mL) solution of isopropyl(1-methyl)indol-3-yl)acetimidate hydrochloride (610 mg, 2.3 mmol) containing triethylamine (9.3 mmol) and 4 A molecular sieves (2.8 g). The reaction was brought to room temperature. After 4 hours, the reaction was quenched with water, washed with 0.5N HCl. The organic layer was separated and concentrated. The residue was dissolved in pyridine (5 mL) cooled to 0° C., and molecular sieves 4 A (7 g) was added followed by triflouroacetic anhydride. The reaction was brought to room temperature and after 2.5 hours and then filtered. The filtrate washed with saturated NaHCO$_3$, water (2×), dried, filtered, and concentrated. The residue was concentrated from toluene (3×) and purified by flash chromatography eluting with 10% acetone/toluene to give the title compound 366 mg (30% yield) of red crystals. 1H-NMR (CDCl3, 250 MHz) δ 1.48 (9H, s), 1.74 (2H, m), 2.02 (2H, m), 2.87 (2H, m), 3.85 (3H, s), 4.29 (3H, m), 6.69 (2H, d), 6.88 (1H, t), 7.07–7.36 (5H, m), 7.51 (1H, s), 7.68 (1H, s), 7.75 (1H, bs).

| Example 6 | IC$_{50}$ (μm) | | | | | | | |
|---|---|---|---|---|---|---|---|---|
| | α | β1 | β2 | γ | δ | ε | ζ | η |
| | 6.1 | 0.22 | 0.082 | 5.3 | 7.3 | 4.4 | >100 | 3 |

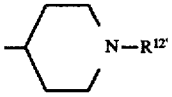

R$^1$
R$^2$ H
R$^{1'}$ CH$_3$
R$^{2'}$ H
R$^{12'}$ t-butoxycarbonyl

EXAMPLE 7

3-(1-[4-(1-t-butoxycarbonyl)-piperidin-4-yl]-3-indolyl)-4-(1-methyl-3-indolyl)-1H-pyrrole-2,5-dione The titled compound was prepared in a manner analogous to Example 6. 1H-NMR (CDCl3, 250 MNz) δ 1.49 (9H, m),

| Example 5 | IC$_{50}$ (μm) | | | | | | | |
|---|---|---|---|---|---|---|---|---|
| | α | β1 | β2 | γ | δ | ε | ζ | η |
| | 0.37 | 0.044 | 0.029 | 0.50 | 0.47 | 2.6 | 42 | 0.15 |

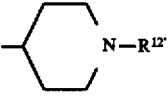

R$^1$
R$^2$ H
R$^{1'}$ CH$_3$
R$^{2'}$ H
R$^{12'}$
C(=NBoc)NHBoc

EXAMPLE 6

3-(1-[4-(1-t-butoxycarbonyl)-piperidinyl]-3-indolyl)-4-(1-methyl-3-indolyl)-1H-pyrrole-2,5-dione To a 0° C. ether (6 mL) solution of 1-t-butoxycarbonyl-4-(1-indolyl)-piperidine (690 mg, 2.3 mmol) was added oxalyl chloride (0.22 mL, 2.5 mmol). After 15 minutes, the precipitant was filtered under argon, washed with ether and 1.79 (2H, m), 2.02 (2H, m), 2.88 (2H, m), 4.27 (3H, m), 6.74 (1H, m), 6.85 (2H, m), 7.07–7.35 (5H, m), 7.59 (1H, s), 7.62 (1H, s), 7.74 (1H, s), 8.67 (1H, bs). MS 510 [M$^+$], calculated. 510 FW.

| Example 7 | IC$_{50}$ (μm) | | | | | | |
|---|---|---|---|---|---|---|---|
| | α | β1 | β2 | γ | δ | ε | ζ | η |
| | 3.3 | 0.23 | 0.10 | 2.8 | 4.1 | 6.3 | 31 | 6.2 |

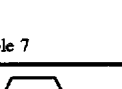

R$^1$
R$^2$ H
R$^{1'}$ H
R$^{2'}$ H
R$^{12'}$ t-butoxy-carbonyl

EXAMPLE 8

3-[1-(1-i-Propyl-piperidin-4-yl)-1H-indol-3-yl]-4-(1-methyl-1H-indol-3-yl)-pyrrole-2,5-dione The title compound was prepared analogously to 3-[1-(1-cyclopropylmethyl-piperidin-4-yl)-1H-indol-3-yl]-4-(1-methyl-1H-indol-3-yl)-pyrrole-2,5-dione.

Yield: 11% of theory. M.Pt.: >250° C.

| Example 8 | IC$_{50}$ (μm) | | | | | | |
|---|---|---|---|---|---|---|---|
| | α | β1 | β2 | γ | δ | ε | ζ | η |
| | 0.34 | 0.019 | 0.026 | 1.3 | 0.97 | 0.39 | 9.3 | 0.13 |

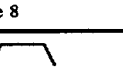

R$^1$
R$^2$ H
R$^{1'}$ CH$_3$
R$^{2'}$ H
R$^{12'}$ CH(CH$_3$)$_2$

EXAMPLE 9

3-[8-(Hydroxymethyl)-6,7,8,9-tetrahydropyrido[1,2-a]indol-10-yl]-4-(1-methyl-3-indolyl)-1H-pyrrole-2,5 dione This compound was prepared as described in EP 0 540 956 A1, and J. Med. Chem., 36(1), 21–29 (1993).

| Example 9 | IC$_{50}$ (μm) | | | | | | |
|---|---|---|---|---|---|---|---|
| | α | β1 | β2 | γ | δ | ε | ζ | η |
| R$^1$R$^2$ CH$_2$CH$_2$CR$^8$R$^9$CH$_2$ | 0.27 | 0.014 | 0.0061 | 1.5 | 0.44 | 3.8 | 9.26 | 0.40 |
| R$^8$ H | | | | | | | | |
| R$^9$ CH$_2$OH | | | | | | | | |
| R$^{1'}$ CH$_3$ | | | | | | | | |
| R$^{2'}$ H | | | | | | | | | structure

| Example 10 | IC$_{50}$ (μM) | | | | | | |
|---|---|---|---|---|---|---|---|
| | α | β1 | β2 | γ | δ | ε | ζ | η |
| R$^1$ 3-(dimethyl-amino)propyl | 0.66 | 0.05 | 0.05 | 1.04 | 0.92 | 0.93 | 23 | 0.09 |
| R$^2$ H | | | | | | | | |
| R$^{1'}$ H | | | | | | | | |
| R$^{2'}$ H | | | | | | | | |

| Example 11 | α | β1 | β2 | γ | δ | ε | ζ | η |
|---|---|---|---|---|---|---|---|---|
| R$^1$ 3-hydroxypropyl | 0.45 | 0.039 | 0.046 | 1.1 | 0.41 | 0.68 | 16 | 0.1 |
| R$^2$ H | | | | | | | | |
| R$^{1'}$ H | | | | | | | | |

The following examples were prepared in a manner analogous to the examples by techniques known in the art and described herein.

| | IC$_{50}$ (μM) | | | | | | | |
|---|---|---|---|---|---|---|---|---|
| R$^{2'}$ H | | | | | | | | |
| Example 12 | α | β1 | β2 | γ | δ | ε | ζ | η |
| R$^1$ CH$_3$<br>R$^2$ H<br>R$^{1'}$ H<br>R$^{2'}$ H | 1.21 | 0.081 | 0.086 | 1.25 | 1 | 0.9 | 8 | 0.52 |
| Example 13 | α | β1 | β2 | γ | δ | ε | ζ | η |
| R$^1$ 3-(dimethyl-amino)propyl<br>R$^2$ H<br>R$^{1'}$ CH$_3$<br>R$^{2'}$ H | 2.3 | 0.14 | 0.06 | 1.7 | 0.93 | 3.6 | 25 | 0.47 |
| Example 14 | α | β1 | β2 | γ | δ | ε | ζ | η |
| R$^1$ benzyl<br>R$^2$ H<br>R$^{1'}$ H<br>R$^{2'}$ H | 13.5 | 1.15 | 1.14 | 25 | 8.8 | 30 | 34 | 4.5 |
| Example 15 | α | β1 | β2 | γ | δ | ε | ζ | η |
| R$^1$ 3-(dimethyl-amino)propyl<br>R$^2$ CH$_3$<br>R$^{1'}$ dimethyl-aminomethyl<br>R$^{2'}$ H | 4.9 | 0.14 | 0.1 | 4 | 3.4 | 5.5 | 37 | 1.3 |
| Example 16 | α | β1 | β2 | γ | δ | ε | ζ | η |
| R$^1$ 3-(dimethyl-amino)propyl<br>R$^2$ CH$_3$ | 39 | 0.7 | 0.6 | 9.2 | 8 | 10 | 40 | 5.6 |

| | IC$_{50}$ (μM) |
|---|---|
| R$^{1'}$ dimethyl-aminomethyl<br>R$^{2'}$ CH$_3$ | |

EXAMPLE 17

3-(1-[3-Cyclopropylamino-1-propyl]-3-indolyl)-4-(1-methyl-3-indolyl)-1H-pyrrole-2,5-dione To a 0° C. solution of trifluoromethanesulfonic acid anhydride (188 mg, 0.67 mmol) in dry methylene chloride (15 mL) was added a solution of 3-[1-(3-hydroxy-propyl)-1H-indol-3-yl)-(1-methyl-1H-indol-3-yl)-pyrrole-2,5-dione (100 mg, 0.25 mmol) in THF (10 mL). After 2 hours, cyclopropylamine (200 μl, 5 mmol) was added and stirring continued over night. The reaction mixture was quenched with water. The organic phase was separated, washed with water (3×), dried, and evaporated. The residual red oil was purified by flash chromatography on silica gel eluting with a methylene chloride/ethanol gradient (98:2–5:5). Evaporation of the eluting solvent gave the title compound (70 mg, 64% yield).

| Example 17 | α | β1 | β2 | γ | δ | ε | ζ | η |
|---|---|---|---|---|---|---|---|---|
| R$^1$ 3-(cyclo-propylamino)-propyl<br>R$^2$ H<br>R$^{1'}$ CH$_3$<br>R$^{2'}$ H | 2.1 | 0.14 | 0.12 | 4.8 | 2.1 | 4.6 | 26 | 0.27 |

Examples 18 to 22 are prepared in a manner analogous to the examples and description provided herein.

| | | α | β1 | β2 | γ | δ | ε | ζ | η |
|---|---|---|---|---|---|---|---|---|---|
| Example 18 | | | | | | | | | |
| R$^1$R$^2$ —CH$_2$CH$_2$CR$^8$R$^9$CH$_2$—<br>R$^8$ H<br>R$^9$ CH$_2$NH$_2$<br>R$^{1'}$ CH$_3$<br>R$^{2'}$ H | | 1.4 | 0.07 | 0.06 | 1.3 | 1.45 | 1.88 | 6.6 | 0.24 |
| Example 19 | | | | | | | | | |
| R$^1$R$^2$ —CH$_2$CH$_2$CR$^8$RCH$_2$—<br>R$^8$ H<br>R$^9$ —CH$_2$N(CH$_3$)$_2$<br>R$^{1'}$ CH$_3$<br>R$^{2'}$ H | | 1.38 | 0.04 | 0.06 | 1.6 | 1.4 | 1.7 | 8.8 | 0.26 |
| Example 20 | | | | | | | | | |
| R$^1$ p-methoxy-phenylmethyl<br>R$^2$ H<br>R$^{1'}$ H<br>R$^{2'}$ H | | 7.8 | 0.46 | 0.44 | 8.7 | 8.8 | 9.3 | 87.8 | ND |

-continued

|  | α | β1 | β2 | γ | δ | ε | ζ | η |
|---|---|---|---|---|---|---|---|---|
| Example 21 | | | | | | | | |
| R¹ 3-propenyl | 0.79 | 0.063 | 0.062 | 3.1 | 0.5 | 1.7 | 14 | 0.3 |
| R² H | | | | | | | | |
| R¹' 3-hydroxy-propyl | | | | | | | | |
| R²' H | | | | | | | | |
| Example 22 | | | | | | | | |
| R¹ 3-hydroxy-propyl | 0.24 | 0.018 | 0.024 | 0.82 | 0.2 | 0.42 | 9.7 | 0.09 |
| R² H | | | | | | | | |
| R¹' 3-hydroxy-propyl | | | | | | | | |
| R²' H | | | | | | | | |

EXAMPLE 23

3-(1-[2-(β-D-2-Deoxyribopyranosyl)-hydroxyethyl]-1-indolyl)-4-(1-methyl-3-indolyl)-1H-pyrrole-2,5-dione 3-[1-(-Acetoxyethyl)-3-indolyl]-4-(1-methyl-3-indolyl-2,5-furandione (*J. Med. Chem.* 1992, Vol. 25, 994, 1 g, 2.3 mmol) was suspended in ethanol (100 mL). Sodium methoxide (5 mL, 5 molar in ethanol) was added. The mixture was stirred at room temperature for 4 hours, acidified with acetic acid, and concentrated. The residue was quenched with water and extracted with ethyl acetate. The organic phase was dried and concentrated to give a residue of 3-[1-(-hydroxyethyl)-3-indolyl]-4-(1-methyl-3-indolyl)-2,5-furandione (0.85 g). The residue was dissolved in methylene chloride (100 mL). Molecular sieves (4 g, 4 Å), silver carbonate (2 g), and silver perchlorate (0.2 g) were added. To this mixture was added dropwise 3,5-di-O-toluyl-2-deoxy-α-D-ribopyranosyl chloride (1 g, 2.5 mmol) (described in *Chem. Ber.* 1960, 2777) dissolved in methylene chloride (80 mL). The mixture was then stirred at room temperature for 24 hours, filtered, and concentrated. To this mixture was added a sodium methanolate solution (1N, 20 mL). After 20 minutes, the reaction mixture was acidified (pH 4) with acetic acid and again concentrated. The residue was dissolved in ethyl acetate and washed (2×) with water, dried, and concentrated. The product (1.4 g) obtained was purified by column chromatography (eluant: toluene/acetone 9:1). Evaporation of the eluant gave a residue (620 mg) that was dissolved in DMF (6 mL) and aqueous ammonia (33%, 6 mL) and heated in an autoclave (150° C.) for 30 minutes. After cooling, the mixture was concentrated. The residue was washed with water and dried to give the title compound (510 mg, 44% yield).

¹H-NMR (DMSO-d₆): 1.9 and 2.3 (2H, m, H-2'ab), 3.7 (2H, m, CH₂), 3.85 (3H, s, NCH₃), 3.9 (3H, s, NCH₃), 4.4 (2H, m, CH₂), 4.6–5.0 (4H, m, sugar H), 6.6–7.9 (10H, m, indole H), 10.9 (1H, s, NH).

| Example 23 | α | β1 | β2 | γ | δ | ε | ζ | η |
|---|---|---|---|---|---|---|---|---|
| | 1.2 | 0.082 | 0.076 | 5.7 | 1.2 | 1.5 | 30 | 0.97 |

R¹
R² H
R¹' CH₃
R²' H

EXAMPLE 24

3-[1-N-(3-(cyclohexylaminecarboxy)-propyl)-indol-3-yl-4-[1-N-(methyl)-indol-3-yl]-1H-pyrrole-2,5-dione To a solution of 100 mg (0.25 mmol) of 3-[1-N-(3-hydroxypropyl)-indol-3-yl]-4-[1-N-(methyl)-indol-3-yl)]-1H-pyrrole-2,5-dione in 5 mL of toluene was added 31 mg (0.25 mmol) cyclohexyl isocyanate and refluxed for 70 hours. The mixture was evaporated, and the residue purified by flash chromatography on silica gel with methylene chloride/ethanol 95:5, yielding 60 mg of a red powder (46% of theory).

| Example 24 | α | β1 | β2 | γ | δ | ε | ζ | η |
|---|---|---|---|---|---|---|---|---|
| | 4.8 | 0.14 | 0.13 | 7.1 | 4.8 | 6.8 | 19 | 1.4 |

R¹
R² H
R¹' CH₃
R²' H

Examples 25 and 31 are prepared in a manner analogous to the examples and description provided herein.

|  |  | α | β1 | β2 | γ | δ | ε | ζ | η |
|---|---|---|---|---|---|---|---|---|---|
| Example 25 | | | | | | | | | |
| $R^1$ | methyl-carbonyloxy propyl | 1 | 0.07 | 0.07 | 1.8 | 1.1 | 1.5 | 18 | 0.28 |
| $R^2$ | H | | | | | | | | |
| $R^{1'}$ | H | | | | | | | | |
| $R^{2'}$ | H | | | | | | | | |
| Example 26 | | | | | | | | | |
| $R^1$ | acetyloxy propyl | 4.2 | 0.01 | 0.015 | 5.2 | 3 | 7 | 34 | 1 |
| $R^2$ | $CH_3$ | | | | | | | | |
| $R^{1'}$ | H | | | | | | | | |
| $R^{2'}$ | H | | | | | | | | |
| Example 27 | | | | | | | | | |
| $R^1$ | 3-hydroxypropyl | 3.9 | 0.08 | 0.08 | 2.9 | 2.4 | 7 | 32 | 2.4 |
| $R^2$ | $CH_3$ | | | | | | | | |
| $R^{1'}$ | H | | | | | | | | |
| $R^{2'}$ | H | | | | | | | | |
| Example 28 | | | | | | | | | |
| $R^1$ | 3-propenyl | 1.98 | 0.18 | 0.17 | 3.3 | 1.2 | 3.2 | 24 | 1 |
| $R^2$ | H | | | | | | | | |
| $R^{1'}$ | H | | | | | | | | |
| $R^{2'}$ | H | | | | | | | | |
| Example 29 | | | | | | | | | |
| $R^1$ | 3-hydroxypropyl | 1.3 | 0.08 | 0.11 | 18 | 1.2 | 11.3 | 27 | 0.54 |
| $R^2$ | H | | | | | | | | |
| $R^{1'}$ | H | | | | | | | | |
| $R^{2'}$ | $CH_3$ | | | | | | | | |
| Example 30 | | | | | | | | | |
| $R^1$ | 3-hydroxypropyl | 18.6 | 0.95 | 0.96 | 86 | 13 | 65 | 70 | 6.6 |
| $R^2$ | $CH_3$ | | | | | | | | |
| $R^{1'}$ | H | | | | | | | | |
| $R^{2'}$ | $CH_3$ | | | | | | | | |
| Example 31 | | | | | | | | | |
| $R^1$ | methylamino propyl | 0.68 | 0.06 | 0.02 | 1.2 | 1 | 1 | 14 | 0.05 |
| $R^2$ | H | | | | | | | | |
| $R^{1'}$ | H | | | | | | | | |
| $R^{2'}$ | H | | | | | | | | |

EXAMPLE 32+33

3-(1-[4-(2,5-Dideoxy-5-azido-α-D-ribofuranosyl)-hydroxybutyl]-3-indolyl)-4-(1-methyl-3-indolyl)-1H-pyrrole-2,5-dione and 3-1(1-[4-(2,5-Dideoxy-5-azido-β-D-ribofuranosyl)-hydroxy-butyl]-3-indolyl-4-(1-methyl-3-indolyl)-1H-pyrrole-2,5-dione-pyrrole-2,5-dione Molecular sieves (3 g, 4 Å) were added to a solution of 3-[1-N-(4-hydroxybutyl)-3-indolyl]-4-[1-N-(methyl)-3-indolyl]-1H-pyrrole-2,5-dione (1.3 g, 3 mmol) and 3-O-acetyl-5-azido-2,5-dideoxy-D-ribosyl acetate (0.8 g, 3.3 mmol) in dry methylene chloride (40 mL). After 1 hour, the mixture was cooled to −25° C. and TMS-OTf (0.05 mL) was added. After 1 hour, the mixture was warmed to room temperature and quenched with triethylamine, filtered, washed with water, dried, and concentrated. The crude product (1.8 g) was dissolved in dioxane (50 mL), and potassium hydroxide (5 g in 50 mL of water) was added. After 18 hours, the reaction mixture was acidified with 2N hydrochloric acid and extracted with ethyl acetate. The organic phase was washed with water, dried, and concentrated. The crude product (1.2 g) obtained was dissolved in DMF (6 mL) and aqueous ammonia (33%, 25 mL, and heated in an autoclave for 2 hours (140° C.). After cooling, the mixture was concentrated, dissolved in ethyl acetate, washed with water, dried, and concentrated. The anomers were purified and separated on silica gel (eluant: toluene/ethanol (8:2) to give 310 mg of the α anomer and 300 mg of the β anomer.).

α anomer $^1$H-NMR (CDCl$_3$): 1.6 (2H, m, CH$_3$), 1.9 (2H, m, CH$_2$), 2.1 (2H, m, H-2'ab), 3.7 (2H, m, CH$_2$), 3.8 (3H, s, NCH$_3$) 4.2 (2H, m, CH$_2$) 5.2 (1H, d, H-1'), 6.7–7.9 10H, indole H β anomer $^1$H-NMR (CDCl$_3$): 1.6 (2H, m, CH$_2$), 1.9 (2H, m, CH$_2$), 2.1 (m, 1H-2'a), 2.2 (m, 1H, H-2'b), 3.8 (2H, m, CH$_2$) 3.9 (3H, s, NCH$_3$) 4.2 2H, m, CH$_2$), 5.15 (1H, d, H-1'), 6.7–7.8 (10H, indole H).

| Example 32 | α | β1 | β2 | γ | δ | ε | ζ | η |
|---|---|---|---|---|---|---|---|---|
| R$^1$  CH$_3$ | 1.2 | 0.045 | 0.047 | 6.7 | 29 | 35 | 64 | 6.7 |
| R$^2$  H | | | | | | | | |
| R$^{1'}$ | | | | | | | | |
| R$^{2'}$  H | | | | | | | | |

| Example 33 | α | β1 | β2 | γ | δ | ε | ζ | η |
|---|---|---|---|---|---|---|---|---|
| R$^1$  CH$_3$ | 1.9 | 0.11 | 0.05 | 4.4 | 3.2 | 5.5 | 26 | 2.6 |
| R$^2$  H | | | | | | | | |
| R$^{1'}$ | | | | | | | | |
| R$^{2'}$  H | | | | | | | | |

EXAMPLE 34

3-(1-[4-(2-Dideoxy-β-D-ribosyl)-hydroxybutyl]-3-indolyl)-4-(1-methyl-3-indolyl)-1H-pyrrole-2,5-dione Molecular sieves (10 g, 4 A) and silver carbonate (5 g) were added to a solution of 3-(1-[4-hydroxybutyl]-3-indolyl)-4-(1-methyl-3-indolyl)-1H-pyrrole-2,5-dione (1.2 g, 2.8 mmol) in absolute methylene chloride (100 mL). The mixture was stirred at room temperature for 1 hour. A solution of 3,5-di-O-toluyl-α-D-2-deoxyribopyranosyl chloride (1.32 g, 3.4 mmol) in absolute methylene chloride (30 mL) was added dropwise. After 18 hours, the reaction mixture was filtered and concentrated. The residue (3.5 g) was dissolved in dioxane (50 mL). Potassium hydroxide (5 g of KOH in 50 mL of water) was added. After 18 hours, the reaction was acidified with 2N HCl and extracted with ethyl acetate. The organic phase was washed with water, dried, and concentrated. The residue (1.1 g) was dissolved in DMF (5 mL) and aqueous ammonia (33%, 20 mL) and heated in an autoclave for 2 hours (140° C.). After the usual workup, the product is purified by column chromatography (eluant: methylene chloride/ethanol 90:10). Yield of α anomer: 320 mg (30%). Yield of β anomer: 410 mg (39%).

β anomer $^1$H-NMR (CDCl$_3$): 1.6 (2H, m, CH$_2$), 1.9 (2H, m, CH$_2$), 2.1 (1H m, H-2'b), 2.2 (1H, m, H-2'a), 3.8 (2H, m, CH$_3$) 3.85 (3H, s, NCH$_3$), 4.2 (2H, m, CH$_3$), 5.2 (1H, d, H-1', 6.7–7.7 (10H, indole H), 8.5 (1H, s, NH).

| Example 34 | α | β1 | β2 | γ | δ | ε | ζ | η |
|---|---|---|---|---|---|---|---|---|
| R$^1$  CH$_3$ | 0.42 | 0.033 | 0.035 | 3.8 | 0.92 | 2.3 | 43 | 1.5 |
| R$^2$  H | | | | | | | | |

| Example 34 | α | β1 | β2 | γ | δ | ε | ζ | η |
|---|---|---|---|---|---|---|---|---|

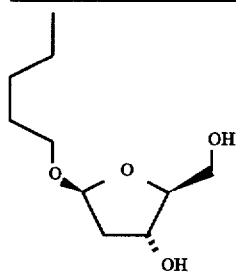

R¹'  
R²' H

EXAMPLE 35

Compound was prepared in a manner analogous to the Examples 32, 33 and 34.

| Example 35 | | α | β1 | β2 | γ | δ | ε | ζ | η |
|---|---|---|---|---|---|---|---|---|---|
| R¹ | CH₃ | 1.3 | 0.045 | 0.036 | 4.2 | 1.8 | 2.5 | 42 | 1.5 |
| R² | H | | | | | | | | |

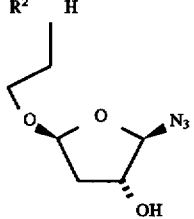

R¹'  
R²' H

EXAMPLE 36

3-(1-[2-(5-Acetamido-2,5-dideoxy-β-D-ribofranosyl)-hydroxyethyl]-3-indolyl-4-(1-methyl-3-indolyl)-1H-pyrrole-2,5-dione Molecular sieves (4.3 g, 4 A) and 1,3-di-O-acetyl-5-azido-2,5-dideoxy-D-ribofuranose (1 g, 4.1 mmol) were added to a solution of 3-[1-(3-hydroxyethyl)-3-indolyl]-4-(1-methyl-3-indolyl)-2,5-furandione (1, g, 3.8 mmol) in methylene chloride (80 mL). After 1 hour, TMS triflate (90 µL) was added. After 3 hours, the reaction was quenched with triethylamine and washed with water. The organic phase was separated, dried, and concentrated. The crude product (1.6 g) obtained was dissolved in ethanol (20 mL) and dioxane (30 mL). Nickel chloride solution (10 mL, 4% in ethanol) was added followed by NaBH₄ (150 mg). After 1 hour, pyridine (30 mL) followed by acetic anhydride (10 mL) was added. After 2 hours, the mixture was concentrated, diluted with ethyl acetate, washed with water, dried, and concentrated. The residue, 0.9 g, was dissolved in dioxane (30 mL) and aqueous ammonia (33%, 100 mL), and heated in an autoclave (130° C.) for 2 hours.

After cooling, the mixture was concentrated, dissolved in ethyl acetate, washed with water, dried, and concentrated. The residue was passed through a column of silica gel (eluant ethanol/methylene chloride (7:3). The α anomer (150 mg) and the β anomer (350 mg) were obtained upon evaporation of the eluant after separation.

β anomer

¹H-NMR (CDCl₃): 1.8 (3H, s, NAC), 2.0 (1H, m, H-2b), 2.2 (1H, m, H-2a), 3.7 (2H, m, CH₂), 3.8 (3H, s, NMe), 4.2 (2H, m, CH₂), 600 (1H, d, H-1), 6.7–7.7 (10H, indol H), 9.1 (1H, s, NH)

| Example 36 | | α | β1 | β2 | γ | δ | ε | ζ | η |
|---|---|---|---|---|---|---|---|---|---|
| R¹ | CH₃ | 1.2 | 0.045 | 0.047 | 6.7 | 2.9 | 3.5 | 64 | 1.5 |
| R² | H | | | | | | | | |
| R¹' | | | | | | | | | |

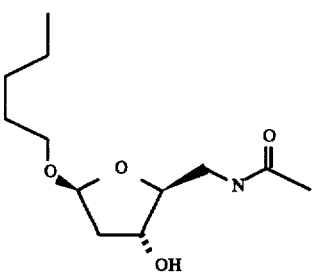

R²' H

EXAMPLE 37

3-(1-(1Acetyl-piperidin-4-yl]-indol-3-yl)-4-(1-methyl-indol-3-yl)-pyrrole-2,5-dione 3-(1-[4-(1-t-butoxycarbonyl)-piperidinyl]-3-indolyl)-4-(1-methyl-3-indolyl)-1H-pyrrole-2,5-dione (120 mg, 0.23 mmol) was added to a solution of ethanethiol (0.27 mL) in trifluoroacetic acid (2.7 mL) precooled to 0° C. with proper stirring. After 30 minutes the reaction mixture was made alkaline by careful addition of saturated aqueous sodium hydrogen carbonate and extracted with ethyl acetate. The organic phase was washed with hydrogen carbonate (2×), brine, water, and dried with sodium sulfate. After stirring overnight the solution was filtered, concentrated, and the residue chromatographed on silica gel eluting with toluene/acetone (50:50). Evaporation of the eluting solvent gave 20 mg of orange red crystals (19% yield). M.Pt.: >293° C.

| Example 37 | IC$_{50}$ (μm) | | | | | | | |
|---|---|---|---|---|---|---|---|---|
| | α | β1 | β2 | γ | δ | ε | ζ | η |
| | 0.3 | 0.009 | 0.02 | 1 | 0.4 | 0.4 | 20 | 0.1 |
| R$^1$ | | | | | | | | |
| R$^2$ | H | | | | | | | |
| R$^{1'}$ | CH$_3$ | | | | | | | |
| R$^{2'}$ | H | | | | | | | |
| R$^{12'}$ | —COCH$_3$ | | | | | | | |

EXAMPLE 38

3-[1-N-(1-methylencarboethyoxy-piperindin-4-yl-)-indol-3-yl)-4-(1-methylindol-3-yl-1H-pyrrole-2,5-dione The reaction was performed under an argon atmosphere and exclusion of moisture.

To a 0° C. solution of 4-(1-indolyl)-1-piperidinoacetic acid ethyl ester (520 mg, 1.8 mmol) in methylene chloride (4 mL) was added oxalyl chloride (0.165 mL, 1.9 mmol) with stirring. After 15 minutes, the reaction was concentrated, and the residue suspended in dry methylene chloride (10 mL). To this suspension was added isopropyl-(1-(methyl)indole-3-yl)-acetimidate hydrochloride (480 m, 1.8 mmol), mol sieves (6 g, 0.4 Å), followed by a solution of triethylamine (1.26 mL, 9 mmol) in methylene chloride (2 mL). The reaction was brought to ambient temperature for 3 hours, recooled to 0° C., and p-toluene sulfonic acid (684 mg, 3.6 mmol) was added in small portions. After 2 hours, the reaction was filtered and the filtrate was washed with NaHCO$_3$ (sat. aq.) (3×), brine (2×) and water (1×), dried, and concentrated. The residue was chromatographed on silica gel eluting with methylene chloride/ethanol (96:4). The material obtained was recrystallized from ether to give the title compound (50 mg, 6% yield) as red crystals. M.Pt.: 247°–252° C.

| Example 38 | IC$_{50}$ (μm) | | | | | | | |
|---|---|---|---|---|---|---|---|---|
| | α | β1 | β2 | γ | δ | ε | ζ | η |
| | 1 | 0.05 | 0.05 | 5 | 3 | 0.4 | >100 | 2 |
| R$^1$ | | | | | | | | |
| R$^2$ | H | | | | | | | |
| R$^{1'}$ | CH$_3$ | | | | | | | |
| R$^{2'}$ | H | | | | | | | |
| R$^{12'}$ | CH$_2$CO$_2$CH$_2$CH$_3$ | | | | | | | |

EXAMPLE 39

3-[1-N-(Cyclopropylmethlene)-piperidin-4-yl-indol-3-yl]-4-(1-N-(methyl)-indol-3-yl)-1H-pyrrole-2,5-dione 1-N-[1-N-(cyclopropylmethylene)-piperidin-4-yl]-indole (460 mg, 1.81 mmol) was suspended in ether (8 mL), and the suspension was filtered. The filtrate was cooled to 0° C. and oxalyl chloride (0.175 mL, 2 mmol) was slowly added. After 30 minutes, the precipitate that formed was collected, washed with a small amount of ether, and resuspended in dry methylene chloride (10 mL). To this suspension was added isopropyl(1-(methyl)indole-3-yl)acetimidate hydrochloride (480 mg, 1.81 mmol), followed by the dropwise addition of triethylamine (1.26 mL, 9.05 mmol) in dry methylene chloride (3 mL). After 3 hours, p-toluene sulfonic acid (1.38 g, 7.25 mmol) was added in several portions (slightly exothermic reaction) and stirring continued for an additional hour. The reaction was quenched by washing with NaHCO$_3$ (sat. aq.) (2×), water (1×), and back extraction of the aqueous phase with methylene chloride. The combined organic solutions were dried, concentrated to a small volume, and the title compound crystallized from the solution. The collected crystals gave the title compound (200 mg, 23% of theory) as a bright orange powder (23% of theory). M.Pt.: >250° C.

| Example 39 | IC$_{50}$ (μm) | | | | | | | |
|---|---|---|---|---|---|---|---|---|
| | α | β1 | β2 | γ | δ | ε | ζ | η |
| | 0.3 | 0.03 | 0.01 | 0.4 | 0.4 | 0.9 | 9 | 0.05 |
| R$^1$ | | | | | | | | |
| R$^2$ | H | | | | | | | |
| R$^{1'}$ | CH$_3$ | | | | | | | |
| R$^{2'}$ | H | | | | | | | |
| R$^{12'}$ | cyclopropyl-methylene | | | | | | | |

EXAMPLE 40

3-[1-Ethyl-piperidin-4-yl)-indol-3-yl]-4-(1-methyl-indol-3-yl)-pyrrole-2,5-dione 1-(1-ethyl-piperidin-4-yl)-indole (350 mg, 1.53 mmol) was dissolved in ether (6 mL), cooled to 0° C. and oxalyl chloride (0.175 mL, 2 mmol) was slowly added. After 30 minutes, the precipitate which formed was collected and suspended in dry methylene chloride (10 mL). To this suspension was added isopropyl(1-methyl)indol-3-yl)

acetimidate hydrochloride (410 mg, 1.53 mmol), followed by the dropwise addition of isopropyl(1-methyl)indol-3-yl) acetimidate (1.07 mL, 7.65 mmol) in dry methylene chloride (3 mL). After 3.5 hours, p-toluene sulfonic acid (1.16 g, 6.12 mmol) was added in several portions (slightly exothermic reaction) and stirring continued for an additional hour. Title compound was isolated as described in Example 39. Recrystallization from dioxane yielded 180 mg of bright orange crystals (26% yield). M. pt.: >250° C.

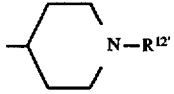

| Example 40 | α | β1 | β2 | γ | δ | ε | ζ | η |
|---|---|---|---|---|---|---|---|---|
| | 0.4 | 0.02 | 0.005 | 0.3 | 0.3 | 0.4 | 7 | 0.04 |

IC$_{50}$ (μm)

R$^1$
R$^2$  H
R$^{1'}$  CH$_3$
R$^{2'}$  H
R$^{12'}$  CH$_2$CH$_3$

EXAMPLE 41

3-{1-[1-N-(3-N,N-(Dimethylamino)propyl)-piperidin-4-yl]-indol-3-yl}-4-(1-methyl-indol-3-yl)-1H-pyrrole-2,5-dione To a stirred 0° C. solution of [3-(4-indol-1-yl-piperidin-1-yl)-propyl]-dimethyl-amine (1 g, 3.25 mmol) in dry methylene chloride (10 mL) was added oxalyl chloride (0.33 mL, 4.2 mmol) and warmed up to ambient temperature for 15 minutes. The reaction was concentrated below 30° C., dissolved in dry toluene (10 mL) and treated with isopropyl (1-methyl)indol-3-yl)acetimidate hydrochloride (930 mg, 3.5 mmol). After slow addition of triethylamine (3 mL, 21 mmol) at 0° C., the mixture was stirred at ambient temperature for 1 hour and then treated with trifluoroacetic acid anhydride (3 mL). After 5 minutes the mixture was carefully quenched with saturated aqueous sodium hydrogen carbonate solution (100 mL). The organic phase was separated, washed with water, dried, and evaporated. The residue solidified on treatment with i-hexane (3×50 mL) and was filtered off. Further purification of the precipitate was accomplished by column chromatography on silica gel eluting with i-propanol/ethyl acetate/triethylamine (47:40:13). The material obtained was triturated with t-butyl methyl ether and dried. Yield: 100 mg of red powder (6% yield).

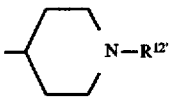

| Example 41 | α | β1 | β2 | γ | δ | ε | ζ | η |
|---|---|---|---|---|---|---|---|---|
| | 3 | 0.2 | 0.1 | 4 | 4 | 1 | 15 | 2 |

IC$_{50}$ (μm)

R$^1$
R$^2$  H
R$^{1'}$  CH$_3$
R$^{2'}$  H
R$^{12'}$  CH$_2$CH$_2$CH$_2$N(CH$_3$)$_2$

EXAMPLE 42

3-[1-(1-Methyl-piperidin-4-yl)-indol-3-yl]-4-(1methyl-indol-3-yl)-1H-pyrrole-2,5-dione The reaction is performed under an inert gas atmosphere with rigorous exclusion of moisture.

To an ice cooled solution of 1-(1-methyl-piperidin-4-yl)-1H-indole (38 g, 0.177 mol) in dry ether (1.2 L) was added oxalyl chloride (16.7 mL, 0.195 mol) dropwise at a rate such that the internal temperature does not exceed 5° C. Stirring at 0° to 5° C. is continued for 30 minutes. A yellow precipitate was isolated by suction filtration, washed with ether (800 mL) and suspended in methylene chloride (1.5 L). The solution was recooled to 0° to 5° C. and treated with isopropyl(1-methyl)indol-3-yl)acetimidate hydrochloride (49.6 g, 0.186 mol) in one portion followed by dropwise addition of triethylamine (123 mL, 0.885 mol). The reaction was brought to ambient temperature and stirred for 3 hours. Anhydrous p-toluene sulfonic acid (152.4 g) was added in several portions with external cooling and stirring was continued for 30 minutes. The mixture was poured into saturated aqueous sodium hydrogen carbonate (2 L) and shaken. A bright orange precipitate (32.2 g) formed which was isolated by suction filtration and washed successively with water, dioxane, and ether. A second crop was isolated by evaporation of the mother liquor and trituration with dioxane (9.4 g). Total yield: 41.6 g (54% of theory). M.Pt.: 316°–318° C.

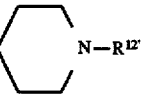

| Example 42 | α | β1 | β2 | γ | δ | ε | ζ | η |
|---|---|---|---|---|---|---|---|---|
| | 0.4 | 0.02 | 0.01 | 0.5 | 0.4 | 0.4 | 4 | 0.05 |

IC$_{50}$ (μm)

R$^1$
R$^2$  H
R$^{1'}$  CH$_3$
R$^{2'}$  H
R$^{12'}$  CH$_3$

EXAMPLE 43

3-[1-(1Methyl-piperidin-4-yl)-indol-3-yl]-4-(1-methyl-indol-3-yl)-1H-pyrrole-2,5-dione hydrochloride An ice cooled solution of 3-[1-(1-methyl-piperidin-4-yl)-1H-indol-3-yl]-4-(1-methyl-1H-indol-3-yl)-pyrrole-2,5-dione (70 g, 0.16 mol) in ethyl acetate (4 L) was saturated with gaseous hydrogen chloride for 3 hours. The precipitate formed was isolated by suction filtration, suspended in methanol (3 L) and stirred for 30 minutes. The mixture turned into a homogenous slurry, which was concentrated and treated with ether (500 mL). The title compound crystallized and was collected by suction filtration. The filter was vacuum dried over night (100° C./0.1 mm. Yield 70 g (92% of theory). M.Pt.: 280°–282° C.

EXAMPLE 44

3-[1-(1-carboxamidine-piperdin-4-yl)-indol-3-yl)-4-(1-methyl-indol-3-yl)-1-pyrrole-2,5-dione

[t-Butoxycarbonylimino-(4-{3-[4-(1-methyl-1H-indol-3-yl)-2,5-dioxo-2,5-dihydro-1H-pyrrole-3-yl]-indol-1-yl}-piperidin-1-yl)-methyl]-carbamic acid t-butyl ester (110 mg, 0.17 mmol) was added to a 0° C. solution of ethanethiol (0.1 mL) in trifluoroacetic acid (1 mL). After 30 minutes, the reaction mixture was brought to ambient temperature for an additional 30 minutes, quenched with saturated aqueous sodium hydrogen carbonate, and diluted with methylene chloride. The organic phase was washed with NaHCO₃ (2×), water, brine, and evaporated. The orange amorphous solid was recrystallized from hot dioxane to give the title compound (40 mg, 50% yield). M.Pt.: >210° C. dec.

| Example 44 | IC₅₀ (μm) | | | | | | | |
|---|---|---|---|---|---|---|---|---|
| | α | β1 | β2 | γ | δ | ε | ζ | η |
| R¹ is CH₃<br>R² is H | 0.042 | 0.005 | 0.005 | 0.082 | 0.1 | 0.36 | 4.8 | 0.005 |

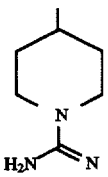

R¹'

R²' is H

EXAMPLE 45

3-(1-Methyl-indol-3-yl)-4-{1-[1-{2,2,2-trifluoro-ethyl)-piperidin-4-yl]-indol-3-yl}-1H-pyrrole-2,5-dione To a stirred 0° C. solution of 1-[1-(2,2,2-trifluoroethyl)-piperidin-4-yl]-indole (180 mg, 0.64 mmol) in dry ether (3 mL) was added oxalyl chloride (0.06 mL, 0.7 mmol). The reaction mixture was warmed to ambient temperature for 30 minutes. An additional amount of oxalyl chloride (0.04 mL, 0.5 mmol) was added. After 30 minutes, a yellow precipitate formed which was filtered with the exclusion of moisture and air, and washed with a small amount of ether. The collected precipitant was dissolved in dry methylene chloride (10 mL) and treated with isopropyl (1-methyl)indol-3-yl)acetimidate hydrochloride (190 mg, 0.71 mmol) followed by slow addition of triethylamine (0.44 mL, 3.2 mmol) at 0° C. After 4 hours at ambient temperature, p-toluene sulfonic acid monohydrate (0.61 g, 3.2 mmol) was added. After 30 minutes the mixture was quenched with saturated aqueous sodium hydrogen carbonate solution (40 mL). The organic phase was separated, washed with water, dried, and evaporated. The residue was recrystallized from hot dioxane and yielded 100 mg of bright orange crystals. Recrystallization of the mother liquor from THF yielded a second crop (60 mg). Yield: 160 mg of bright orange crystals (49% of theory) M.Pt.: >250° C.

| Example 45 | α | β1 | β2 | γ | δ | ε | ζ | η |
|---|---|---|---|---|---|---|---|---|
| R¹ is CH₃<br>R² is H | >100 | 0.13 | 0.037 | >100 | 69 | >100 | >100 | >100 |

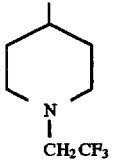

R²' is H

EXAMPLE 46

3-{1-[1(2,2,3,3,4,4,4-Heptafluoro-butyl)-piperidin-4-yl]-indol-3-yl}-4-(1-methyl-indol-3-yl)-1H-pyrrole-2,5-dione To a stirred 0° C. solution of 1-(4,4,4,3,3,2,2-heptafluorobutyl)-4-(1-indolyl)-piperidine (430 mg, 1.12 mmol) in dry ether (5 mL) was added oxalyl chloride (0.11 mL, 1.23 mmol). After 1 hour at room temperature, a yellow precipitate formed. The precipitant was collected by filtration under Ar, washed with ether, suspended in dry methylene chloride (10 mL) and treated with isopropyl(1-methyl) indol-3-yl)acetimidate hydrochloride (300 mg, 1.12 mmol). To this suspension was added triethylamine (0.78 mL, 5.6 mmol) in dry methylene chloride (3 mL) at 0° C. The reaction was stirred at ambient temperature for 3 hours and treated with p-toluene sulfonic acid monohydrate (slightly exothermic) (0.86 g, 4.5 mmol). After 30 minutes, the reaction was carefully quenched with saturated aqueous sodium hydrogen carbonate solution (30 mL). The organic phase was separated, washed with saturated aqueous sodium hydrogen carbonate solution, water, brine, dried, and evaporated. The residue was crystallized from an ethereal solution. Yield: 260 mg of bright orange crystals (38% of theory). M.Pt.: 231°–234° C.

| Example 46 | IC₅₀ (μm) | | | | | | | |
|---|---|---|---|---|---|---|---|---|
| | α | β1 | β2 | γ | δ | ε | ζ | η |
| 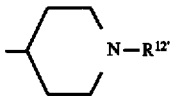 | >100 | 3.0 | 0.46 | >100 | >100 | >100 | >100 | >100 |

R¹<br>R² H<br>R¹' CH₃<br>R²' H<br>R¹²' CH₂CF₂CF₃

Examples 47 to 67 were prepared in a manner analogous to the examples and description provided herein.

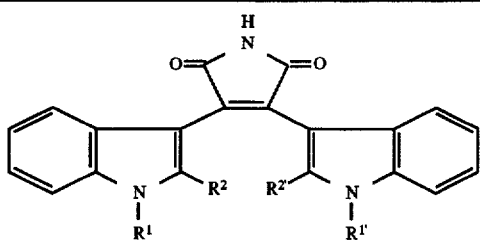
| Example 47 | IC$_{50}$ (μm) | | | | | | | |
|---|---|---|---|---|---|---|---|---|
| | α | β1 | β2 | γ | δ | ε | ζ | η |
| | 1 | 0.1 | 0.05 | 4 | 2 | 3 | 52 | 0.5 |
R$^1$ 
R$^2$ H
R$^{1'}$ CH$_3$
R$^{2'}$ H
R$^{12'}$ CH$_2$C$_6$H$_5$
| Example 48 | IC$_{50}$ (μm) | | | | | | | |
|---|---|---|---|---|---|---|---|---|
| | α | β1 | β2 | γ | δ | ε | ζ | η |
| | 2 | 0.05 | 0.04 | 5 | 2 | 2 | >100 | 2 |
R$^1$
R$^2$ H
R$^{1'}$ CH$_3$
R$^{2'}$ H
R$^{12'}$ 2-pyridine
| Example 49 | IC$_{50}$ (μm) | | | | | | | |
|---|---|---|---|---|---|---|---|---|
| | α | β1 | β2 | γ | δ | ε | ζ | η |
| | 0.8 | 0.03 | 0.03 | 2 | 1 | 0.3 | 8 | 0.4 |
R$^1$
R$^2$ H
R$^{1'}$ CH$_3$
R$^{2'}$ H
R$^{12'}$ CH$_2$-2-pyridine
| Example 50 | IC$_{50}$ (μm) | | | | | | | |
|---|---|---|---|---|---|---|---|---|
| | α | β1 | β2 | γ | δ | ε | ζ | η |
| | 0.3 | 0.03 | 0.02 | 0.6 | 0.5 | 0.5 | 3 | 0.1 |
R$^1$
R$^2$ H
R$^{1'}$ H
R$^{2'}$ H
R$^{12'}$ H -continued

| Example 51 | IC$_{50}$ (μm) | | | | | | | |
|---|---|---|---|---|---|---|---|---|
| | α | β1 | β2 | γ | δ | ε | ζ | η |
| | 0.2 | 0.02 | 0.01 | 0.5 | 0.4 | 0.05 | 5 | 0.04 |

R$^1$ = piperidine-N—R$^{12'}$

| | |
|---|---|
| R$^2$ | H |
| R$^{1'}$ | H |
| R$^{2'}$ | H |
| R$^{12'}$ | CH$_3$ |

| Example 52 | IC$_{50}$ (μm) | | | | | | | |
|---|---|---|---|---|---|---|---|---|
| | α | β1 | β2 | γ | δ | ε | ζ | η |
| | 0.3 | 0.03 | 0.03 | 2 | 0.4 | 1 | 4 | 0.2 |

R$^1$ = piperidine-N—R$^{12'}$

| | |
|---|---|
| R$^2$ | H |
| R$^{1'}$ | CH$_3$ |
| R$^{2'}$ | H |
| R$^{12'}$ | H |

| Example 53 | IC$_{50}$ (μm) | | | | | | | |
|---|---|---|---|---|---|---|---|---|
| | α | β1 | β2 | γ | δ | ε | ζ | η |
| R$^1$ | 3.2 | 0.41 | 0.23 | 4.3 | 3.5 | 6.6 | 51 | 1.7 | fumarate salt

| | |
|---|---|
| R$^2$ | H |
| R$^{1'}$ | CH$_3$ |
| R$^{2'}$ | H |

| Example 54 | IC$_{50}$ (μm) | | | | | | | |
|---|---|---|---|---|---|---|---|---|
| | α | β1 | β2 | γ | δ | ε | ζ | η |
| R$^1$ | 6.7 | 1.1 | 0.34 | 15 | 7.9 | 4.3 | 37 | 2.5 |

Acetate salt

| | |
|---|---|
| R$^2$ | H |
| R$^{1'}$ | CH$_3$ |
| R$^{2'}$ | H |

| Example 55 | IC$_{50}$ (μm) | | | | | | | |
|---|---|---|---|---|---|---|---|---|
| | α | β1 | β2 | γ | δ | ε | ζ | η |
| R$^1$ | 2.3 | 0.26 | 0.05 | 4.2 | 0.95 | 6.6 | 45 | 1.2 |

| | |
|---|---|
| R$^2$ | H |
| R$^{1'}$ | CH$_3$ |

-continued

| | | | | | | | | |
|---|---|---|---|---|---|---|---|---|
| R²' | H | | | | | | | |

Example 56

| | IC$_{50}$ (μm) | | | | | | |
|---|---|---|---|---|---|---|---|
| | α | β1 | β2 | γ | δ | ε | ζ | η |

R¹ = [structure: tetrahydrofuran with HO-CH2, HO, and O-(CH2)4, α,β-D]

1.6  0.069  0.039  3.2  0.93  2.4  49  1.3

R² H
R¹' CH₃
R²' H

Example 57

| | IC$_{50}$ (μm) | | | | | | |
|---|---|---|---|---|---|---|---|
| | α | β1 | β2 | γ | δ | ε | ζ | η |

R¹ = [structure: pyranose with N₃-CH2, HO, OH, OH, O-propyl]

10  1.6  0.36  NA  9.0  >100  >100  4.0

R² H
R¹' CH₃
R²' H

Example 58

| | IC$_{50}$ (μm) | | | | | | |
|---|---|---|---|---|---|---|---|
| | α | β1 | β2 | γ | δ | ε | ζ | η |

R¹ = [structure: tetrahydrofuran with N₃-CH2, HO, O-propyl, α-L]

4.9  0.24  0.27  38  4.5  12  46  2.5

R² H
R¹' CH₃
R²' H

[structure: bisindolylmaleimide core with NH maleimide, two indoles with N-R¹ and N-R¹']

Example 59

| | IC$_{50}$ (μm) | | | | | | |
|---|---|---|---|---|---|---|---|
| | α | β1 | β2 | γ | δ | ε | ζ | η |

R¹ is CH₃

4.5  0.20  0.11  9.0  2.8  31  48  1.6

R¹' = [structure: pyranose with HO-CH2, HO, N₃, OH, O-propyl linker]

-continued
| Example 60 | IC$_{50}$ ($\mu$m) | | | | | | | |
|---|---|---|---|---|---|---|---|---|
| | α | β1 | β2 | γ | δ | ε | ζ | η |
| R$^1$ is CH$_3$ | 4.5 | 0.18 | 0.042 | 24 | 7.4 | 91 | 75 | 3.6 |
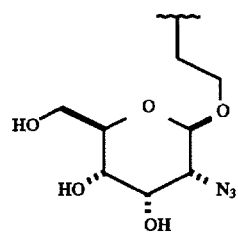
R$^{1'}$
| Example 61 | IC$_{50}$ ($\mu$m) | | | | | | | |
|---|---|---|---|---|---|---|---|---|
| | α | β1 | β2 | γ | δ | ε | ζ | η |
| R$^1$ is CH$_3$ | 3.6 | 0.16 | 0.041 | 4.8 | 3.2 | 20 | 20 | 0.75 |
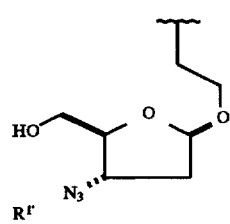
R$^{1'}$
| Example 62 | IC$_{50}$ ($\mu$m) | | | | | | | |
|---|---|---|---|---|---|---|---|---|
| | α | β1 | β2 | γ | δ | ε | ζ | η |
| R$^1$ is CH$_3$ | 4.4 | 0.20 | 0.10 | 5.2 | 3.9 | 42 | 41 | 2.6 |
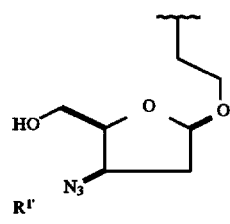
R$^{1'}$
| Example 63 | IC$_{50}$ ($\mu$m) | | | | | | | |
|---|---|---|---|---|---|---|---|---|
| | α | β1 | β2 | γ | δ | ε | ζ | η |
| R$^1$ is CH$_3$ | 1.7 | 0.13 | 0.049 | 4.0 | 1.6 | 3.6 | 50 | 0.14 |
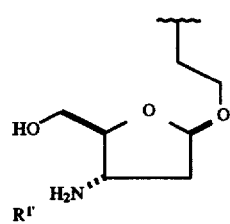
R$^{1'}$
| Example 64 | IC$_{50}$ ($\mu$m) | | | | | | | |
|---|---|---|---|---|---|---|---|---|
| | α | β1 | β2 | γ | δ | ε | ζ | η |
| R$^1$ is CH$_3$ | 0.16 | 0.005 | 0.005 | 0.28 | 0.16 | 0.80 | 50 | 0.040 |

|  |  |
|---|---|
| R1' |  |

| Example 65 | IC₅₀ (μm) | | | | | | | |
|---|---|---|---|---|---|---|---|---|
|  | α | β1 | β2 | γ | δ | ε | ζ | η |
|  | 8.1 | 0.39 | ND | 30 | 8.4 | ND | 47 | 3.4 |

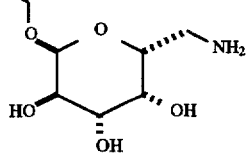

R¹  
Fumarate salt

R¹'  CH₃

| Example 66 | IC₅₀ (μm) | | | | | | | |
|---|---|---|---|---|---|---|---|---|
|  | α | β1 | β2 | γ | δ | ε | ζ | η |
|  | 9.0 | 0.24 | ND | 30 | 4.4 | ND | 37 | 3.0 |

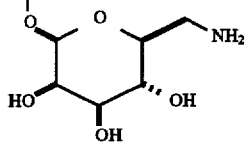

R¹  
Fumarate salt

R¹'  CH₃

| Example 67 | IC₅₀ (μm) | | | | | | | |
|---|---|---|---|---|---|---|---|---|
|  | α | β1 | β2 | γ | δ | ε | ζ | η |
|  | 6.6 | 0.30 | 0.20 | 8.2 | 4.1 | 38 | 47 | 2.6 |

R¹  
Fumarate salt

R¹'  CH₃

EXAMPLE 68

3-(1-Methyl-indol-3-yl)-4-[1-(1-methyl-piperidin-4-ylmethylene)-indol-3-yl]-1H-pyrrole-2,5-dione To a stirred 0° C. solution of 1-(1-methyl-piperidin-4-yl)-indole (420 mg, 1.84 mmol) in dry ether (5 mL) was added oxalyl chloride (0.17 mL, 2.02 mmol). The resulting precipitant was isolated as previously described, and reacted with isopropyl-1-methylindole-3-acetamidate in the same procedure as previously described to produce the title compound as a residue. The residue was chromatographed on silica gel eluting with toluene/acetone (95:5). Evaporation of the eluant and recrystallized from di-i-propyl ether gave the purified title compound. Yield: 210 mg of bright orange crystals (25% of theory). M. pt.: 228° C. (dec.).

| Example 68 | IC₅₀ (μm) | | | | | | | |
|---|---|---|---|---|---|---|---|---|
| | α | β1 | β2 | γ | δ | ε | ζ | η |
| R¹' | 1.4 | 0.047 | 0.033 | 2.4 | 1.9 | 4.6 | 9.8 | 0.11 |

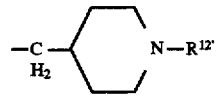

| R¹ | CH₃ |
| R¹²' | CH₃ |

EXAMPLE 69

3-[1-(1-N-ethycarbomate-piperidin-4-yl-methylene)-indol-3-yl]-4-[1-methyindol-3-yl]-1H-pyrrole-2,5-dione A solution containing 4-{3-[4-(1-methyl-1H-indol-3-yl)-2,5-dioxo-2,5-dihydro-1H-furan-3-yl]-indol-1-ylmethyl}-piperidine-1-carboxylic acid ethyl ester (140 mg, 0.275 mmol) and 0.4 mL 33% aqueous ammonia in DMF (1.2 mL) was heated to 140° C. for 2 hours in a sealed vessel, cooled down and evaporated. The residue was dissolved in methylene chloride (20 mL) and washed with water (4×25 mL), dried, and evaporated. 140 mg of bright red powder (theoretical yield). M.Pt.: 104°–106° C.

| Example 69 | IC₅₀ (μm) | | | | | | | |
|---|---|---|---|---|---|---|---|---|
| | α | β1 | β2 | γ | δ | ε | ζ | η |
| R¹ is CH₃ | 6.5 | 0.39 | 0.21 | 8.2 | 7.3 | >100 | >100 | 3.1 |

R¹'

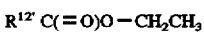

R¹²' C(=O)O—CH₂CH₃

The following compound was prepared in an analogous manner.

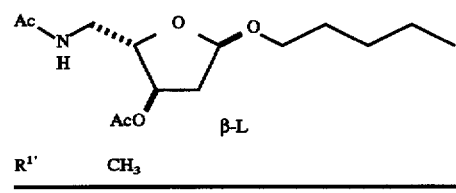

| Example 70 | IC₅₀ (μm) | | | | | | | |
|---|---|---|---|---|---|---|---|---|
| | α | β1 | β2 | γ | δ | ε | ζ | η |
| R¹ | 3.3 | 0.32 | 0.19 | 3.0 | 3.2 | 70 | 37 | 1.4 |

| R¹' | CH₃ |

EXAMPLE 71

3-[1-(Benzyl-pyrrolidin-4-yl)-indol-3-yl)-4-(1-methyl-indol-3-yl)-1H-pyrrole-2,5-dione The title compound was prepared analogous to Example 66. Purification was accomplished by HPLC in silica gel with a methylene chloride/ethanol gradient 99:1 to 98:2. Yield: 6% of theory. MS: 500 (M+), 341, 303, 276, 159, 91 (100%).

| | $IC_{50}$ ($\mu m$) | | | | | | | |
|---|---|---|---|---|---|---|---|---|
| Example 71 | α | β1 | β2 | γ | δ | ε | ζ | η |
| $R^1$ is $CH_3$ | 3.8 | 0.022 | 0.024 | 3.5 | 4.2 | 9.4 | >100 | 0.042 |

EXAMPLE 72

3-[1-Benzhydryl-azetidin-3-yl)-indol-3-yl)-4-(1-methyl-indol-3-yl)-1H-pyrrole-2,5-dione The title compound was prepared analogous to Example 66. Purification was accomplished by HPLC on silica gel with a methylene chloride/ethanol gradient 99:1 to 98:2. Yield 3% of theory. M.Pt.: 102°–105° C.

| | $IC_{50}$ ($\mu m$) | | | | | | | |
|---|---|---|---|---|---|---|---|---|
| Example 72 | α | β1 | β2 | γ | δ | ε | ζ | η |
| $R^1$ is $CH_3$ | >100 | 9.1 | 2.7 | 90 | >100 | >100 | 49 | 0.042 |

The compounds of Formula I, II, III and IV are preferably formulated prior to administration. Therefore, yet another embodiment of the present invention is a pharmaceutical formulation comprising a compound of Formula II, III, and IV, and one or more pharmaceutically acceptable carriers, diluents or excipients.

The present pharmaceutical formulations are prepared by known procedures using well known and readily available ingredients. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient. The compositions are preferably formulated in a unit dosage form, each dosage containing from about 1 to about 500 mg, more usually about 5 to about 300 mg, of the active ingredient. However, it will be understood that the therapeutic dosage administered will be determined by the physician in the light of the relevant circumstances including the condition to be treated, the choice of compound to be administered and the chosen route of administration, and therefore the above dosage ranges are not intended to limit the scope of the invention in any way. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

In addition to the above formulations, the compounds of the present invention may be administered topically. Topical formulations are ointments, creams, and gels.

Ointments generally are prepared using either (1) an oleaginous base, i.e., one consisting of fixed oils or hydrocarbons, such as white petrolatum or mineral oil, or (2) an absorbent base, i.e., one consisting of an anhydrous substance or substances that can absorb water, for example anhydrous lanolin. Customarily, following formation of the base, whether oleaginous or absorbent, the active ingredient (compound) is added to an amount affording the desired concentration.

Creams are oil/water emulsions. They consist of an oil phase (internal phase), comprising typically fixed oils, hydrocarbons, and the like, such as waxes, petrolatum, mineral oil, and the like, and an aqueous phase (continuous phase), comprising water and any water-soluble substances, such as added salts. The two phases are stabilized by use of an emulsifying agent, for example, a surface active agent, such as sodium lauryl sulfate; hydrophilic colloids, such as acacia colloidal clays, veegum, and the like. Upon formation of the emulsion, the active ingredient (compound) customarily is added to an amount to achieve the desired concentration.

Gels comprise a base selection from an oleaginous base, water, or an emulsion-suspension base. To the base is added a gelling agent that forms a matrix in the base, thus increasing its viscosity. Examples of gelling agents are hydroxypropyl cellulose, acrylic acid polymers, and the like. Customarily, the active ingredient (compounds) is added to the formulation at the desired concentration at a point preceding addition of the gelling agent.

The amount of compound incorporated into a topical formulation of invention is not critical; the concentration should only be a range sufficient to permit ready application of the formulation to the an affected tissue area in an amount that will deliver the desired amount of compound. The customary amount of topical formulation to be applied to an affected tissue will depend upon an affected tissue size and concentration of compound in the formulation. Generally, the formulation will be applied to the an affected tissue in an amount affording from about 1 to about 500 µg compound per cm² of an affected tissue. Preferably, the applied amount of compound will range from about 30 to about 300 µg/cm², more preferably, from about 50 to about 200 µg/cm², and, most preferably, from about 60 to about 100 µg/cm².

The following formulation examples are illustrative only and are not intended to limit the scope of the invention in any way.

Formulation 1

Hard gelatin capsules are prepared using the following ingredients:

|  | Quantity (mg/capsule) |
|---|---|
| Active ingredient | 250 |
| starch, dried | 200 |
| magnesium stearate | 10 |
| Total | 460 mg |

The above ingredients are mixed and filled into hard gelatin capsules in 460 mg quantities.

Formulation 2

A tablet is prepared using the ingredients below:

|  | Quantity (mg/capsule) |
|---|---|
| Active ingredient | 250 |
| cellulose, microcrystalline | 400 |
| silicon dioxide, fumed | 10 |
| stearic acid | 5 |
| Total | 665 mg |

The components are blended and compressed to form tablets each weighing 665 mg.

Formulation 3

An aerosol solution is prepared containing the following components:

|  | Quantity (mg/capsule) |
|---|---|
| Active ingredient | 0.25 |
| ethanol | 29.75 |
| Propellant 22 | 70.00 |
| (chlorodifluoromethane) |  |
| Total | 100.0 |

The active compound is mixed with ethanol. The mixture is added to a portion of the Propellant 22, cooled to −30° C. and transferred to a filling device. The required amount is then fed to a stainless steel container and diluted with the remainder of the propellant. The valve units are then fitted to the container.

Formulation 4

Tablets each containing 60 mg of active ingredient are made as follows:

|  | Quantity (mg/capsule) |
|---|---|
| Active ingredient | 60 mg |
| starch | 45 mg |
| microcrystalline cellulose | 35 mg |
| polyvinylpyrrolidone (as 10% solution in water) | 4 mg |
| sodium carboxymethyl starch | 4.5 mg |
| magnesium stearate | 0.5 mg |
| talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

61

Formulation 5

Capsules each containing 80 mg of medicament are made as follows:

|  | Quantity (mg/capsule) |
| --- | --- |
| Active ingredient | 80 mg |
| starch | 59 mg |
| microcrystalline cellulose | 59 mg |
| magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

Formulation 6

Suppositories each containing 225 mg of active ingredient may be made as follows:

|  | Quantity (mg/capsule) |
| --- | --- |
| Active ingredient | 225 mg |
| saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions each containing 50 mg of medicament per 5 mL dose are made as follows:

|  | Quantity (mg/capsule) |
| --- | --- |
| Active ingredient | 50 mg |
| sodium carboxymethyl cellulose | 50 mg |
| syrup | 1.25 mL |
| benzoic acid solution | 0.10 mL |
| flavor | q.v. |
| color | q.v. |
| purified water to total | 5 mL |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

Formulation 8

An intravenous formulation may be prepared as follows:

|  | Quantity (mg/capsule) |
| --- | --- |
| Active ingredient | 250 mg |
| isotonic saline | 1000 mg |

The solution of the above ingredients is administered intravenously at a rate of 1 mL per minute to a subject in need of treatment.

We claim:

1. A compound of the formula:

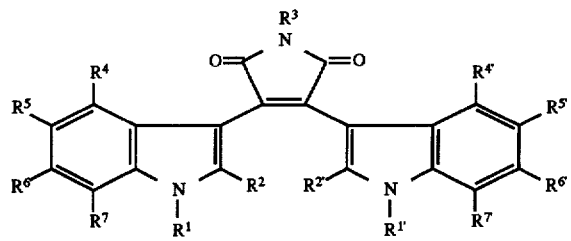

wherein:

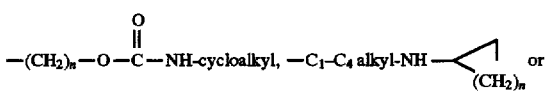

$R^1$ is —$(CH_2)_m$—O—glycosyl; m=2, 3, or 4;

$R^{1'}$ is hydrogen, $C_1$-$C_4$ alkyl, cyclopropylmethyl, aminoalkyl, monoalkylaminoalkyl, or dialkylaminoalkyl;

$R^2$ and $R^{2'}$ are independently hydrogen, alkyl, alkoxyalkyl, hydroxyalkyl, $C_1$-$C_3$ alkylthio, S(O) $C_1$-$C_3$ alkyl, $CF_3$;

$R^3$ is hydrogen or $CH_3CO$—;

$R^4$, $R^{4'}$, $R^5$, $R^{5'}$, $R^6$, $R^{6'}$, $R^7$ and $R^{7'}$ are independently hydrogen, halogen, alkyl, hydroxy, alkoxy, —COO ($C_1$-$C_3$ alkyl), $CF_3$, nitro, amino, acetylamino, monoalkylamino, dialkylamino, alkylthio, $C_1$-$C_3$ alkylthio, or $S(O)C_1$-$C_3$ alkyl;

n is 1, 2, 3, 4, 5 or 6; or pharmaceutically acceptable salts or solvates thereof.

2. A compound of claim 1 wherein $R^3$, $R^4$, $R^{4'}$, $R^5$, $R^{5'}$, $R^6$, $R^{6'}$, $R^7$ and $R^{7'}$ are hydrogen.

3. A method for treating diabetic complications, which comprises administering to a mammal in need of such treatment a pharmaceutically effective amount of a compound of claim 1.

4. A method for treating diabetic complications, which comprises administering to a mammal in need of such treatment a pharmaceutically effective amount of a compound of claim 1.

5. A pharmaceutical formulation comprising a compound of claim 1 and one or more pharmaceutically acceptable carriers, diluents or excipients therefor.

6. A pharmaceutical formulation comprising a compound of claim 2 and one or more pharmaceutically acceptable carriers, diluents or excipients therefor.

* * * * *

UNITED STATES PATENT AND TRADEMARK OFFICE
CERTIFICATE OF CORRECTION

PATENT NO. : 5,672,618  
DATED : September 30, 1997  
INVENTOR(S) : William F. Heath, Jr., et al Page 1 of 2

It is certified that error appears in the above-identified patent and that said Letters Patent is hereby corrected as shown below:

Column 21, line 33, replace the phrase "Methyl-3-O-acetyl-5-azido-2,5-dideoxy-7-D-ribose" with the phase --Methyl-3-O-acetyl-5-azido-2,5-dideoxy-D-ribose --.

Column 26, line, 25, replace the number "3" at the end of the line with -- .3 --.

Column 30, line 24, insert the phrase "4-" following the phrase "1H-indol-3-yl)-".

Column 30, line 31, please replace the number "5:5" with the number "95:5".

Column 30, line 63, under Example 20, please replace the number "87.8" with the number "37.8".

UNITED STATES PATENT AND TRADEMARK OFFICE
CERTIFICATE OF CORRECTION

PATENT NO. : 5,672,618
DATED : September 30, 1997
INVENTOR(S) : William F. Heath, Jr., et al It is certified that error appears in the above-identified patent and that said Letters Patent is hereby corrected as shown below:

Column 31, line 24, replace the phrase "1-indolyl)-4-(1-methyl-3-indolyl)" with the phrase "3-indolyl)-4-(1-methyl-3-indolyl)".

Column 40, line 18, insert the phrase "(1-N" following the "3-(1-N-".

Column 40, line 60, insert the phrase "(1-following the phrase "3-[1-".

Signed and Sealed this

Ninth Day of January, 2001

Attest:

Q. TODD DICKINSON

*Attesting Officer*  *Commissioner of Patents and Trademarks*